(12) United States Patent
Davison et al.

(10) Patent No.: US 7,231,922 B2
(45) Date of Patent: Jun. 19, 2007

(54) APPARATUS, SYSTEM AND METHOD FOR TREATING DRY EYE CONDITIONS AND PROMOTING HEALTHY EYES

(76) Inventors: Suzanne Davison, 40485 MHS Rd., #310, Murrieta, CA (US) 92563; Roy Paulson, 46752 Rainbow Canyon Rd., Temecula, CA (US) 92592

(*) Notice: Subject to any disclaimer, the term of this patent is extended or adjusted under 35 U.S.C. 154(b) by 0 days.

(21) Appl. No.: 11/378,949

(22) Filed: Mar. 16, 2006

(65) Prior Publication Data

US 2006/0157064 A1    Jul. 20, 2006

Related U.S. Application Data

(63) Continuation-in-part of application No. 10/632,188, filed on Jul. 30, 2003, now abandoned.

(51) Int. Cl.
*A61F 9/00* (2006.01)
*G02C 1/00* (2006.01)

(52) U.S. Cl. .................... 128/858; 351/41; 351/158

(58) Field of Classification Search ............... 128/858; 351/106, 45, 41, 51, 52, 158, 24; 2/15, 426, 2/431, 440, 442
See application file for complete search history.

(56) References Cited

U.S. PATENT DOCUMENTS

| | | | | |
|---|---|---|---|---|
| 4,709,695 A | * | 12/1987 | Kohn et al. | 128/132 R |
| 6,641,264 B1 | * | 11/2003 | Schwebel | 351/62 |
| 6,721,963 B1 | * | 4/2004 | Kawashima | 2/426 |

* cited by examiner

*Primary Examiner*—Justine R. Yu
*Assistant Examiner*—Shumaya B. Ali
(74) *Attorney, Agent, or Firm*—Donn K. Harms

(57) ABSTRACT

An eyewear apparatus for treating dry eye conditions featuring a pair of curved eyecups having interior cavities for providing treatment to the eyes when worn. Each interior cavity has a sidewall surface adapted to removably engage with the perimeter edge of a moisture pad which may be mounted therein to provide moisture, aroma, or medicinal treatment to the eye. An ocular cavity formed in the moisture pads provides a separate treatment chamber to each of the two eyes of a user. Heat or cold may also be provided to the ocular chamber through temperature components which mount to the moisture pad or in a gap between the moisture pad and the front of the interior cavity.

24 Claims, 12 Drawing Sheets

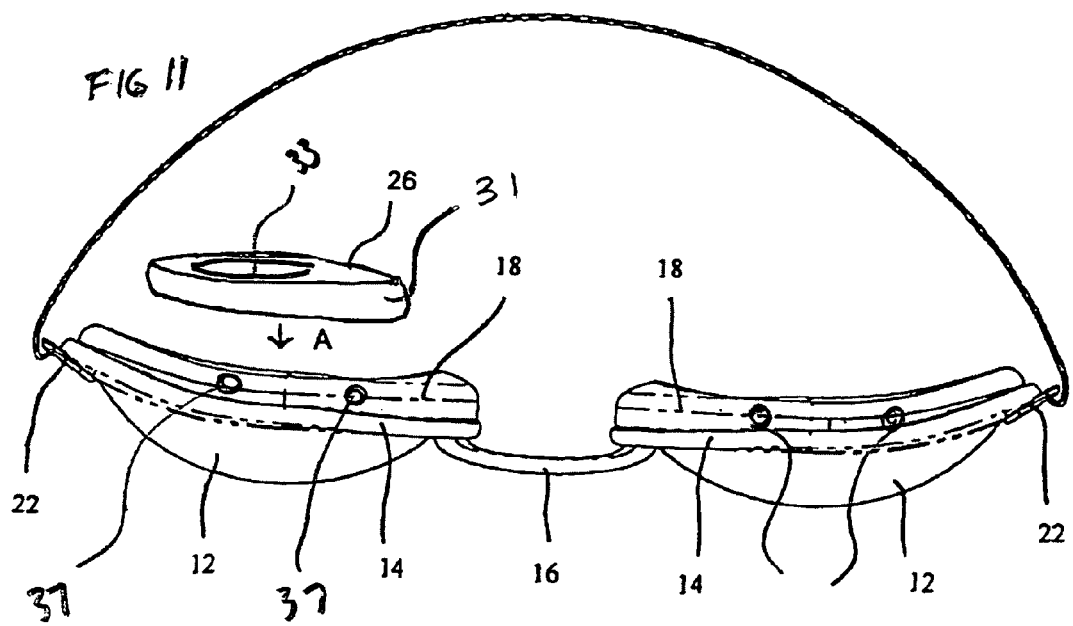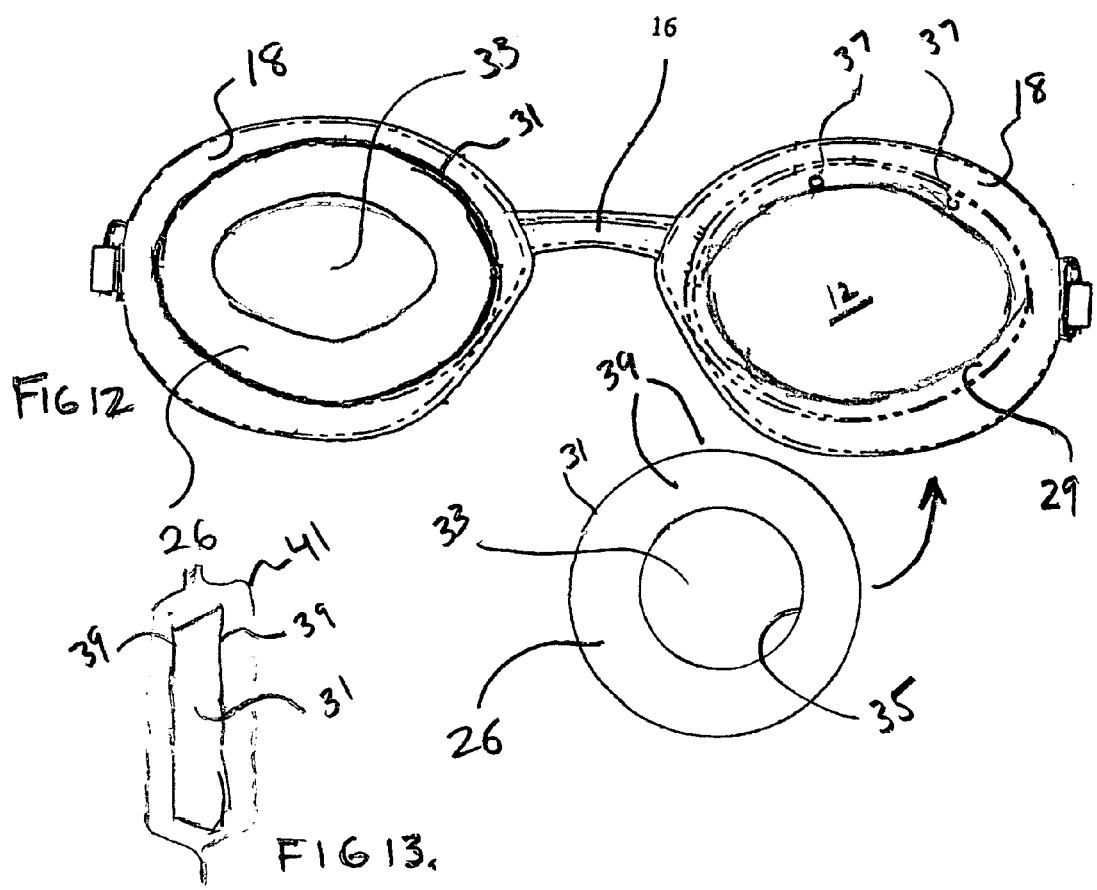

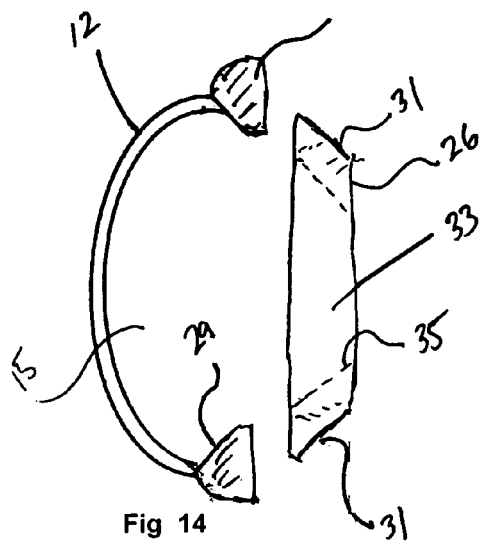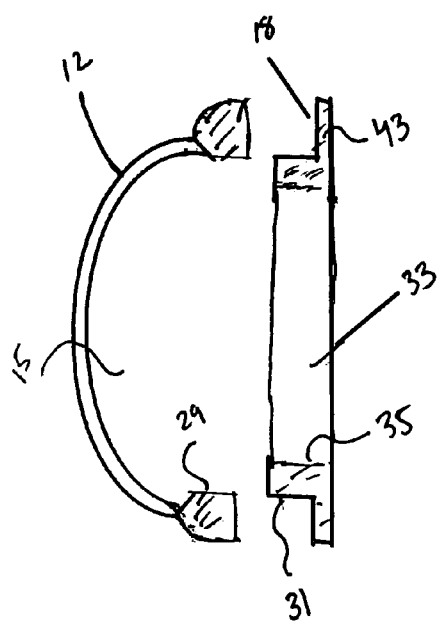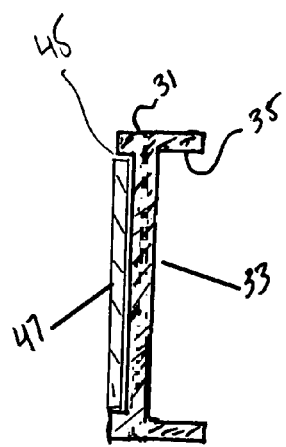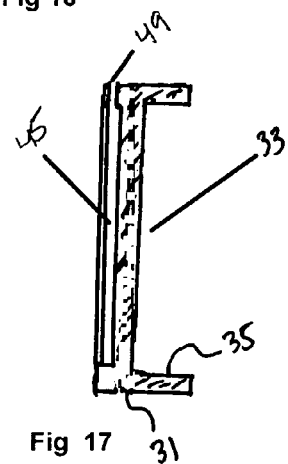

APPARATUS, SYSTEM AND METHOD FOR TREATING DRY EYE CONDITIONS AND PROMOTING HEALTHY EYES

FIELD OF THE INVENTION

This application is a Continuation-in-Part Application from U.S. patent application Ser. No. 10/632,188 filed on Jul. 30, 2003 now abandoned, and currently pending. This invention relates generally to an apparatus, system and method for treating dry and irritated eye conditions. Particularly, this invention relates to an apparatus constructed and adapted to help control, maintain, and/or increase the temperature and humidity in an ocular cavity positioned to surround the eye to aid in limiting evaporation of natural and/or artificial tears, which aids in thickening of the lipid layer, thereby improving the overall health of the eye. This invention also relates to an apparatus, system and method that provides for controlled application of medicine or additional moisture to the eyes employing removably engageable pads adapted to operatively position an ocular cavity to communicate moisture or medicine or both to the eye. Also provided are a means to communicate heat or cold to the eye using pad engageable components capable of being heated or chilled prior to engagement therein.

BACKGROUND OF THE INVENTION

Approximately 60 million Americans suffer from dry eye conditions. Of these, approximately 10 million Americans have been diagnosed with severe dry eye conditions, e.g., Dry Eye Syndrome or Chronic Dry Eye Disease (CDED), both clinically known as keratoconjuctivitis sicca. CDED is a condition that results from inflammation of the eye as well as inflammation of the tear-producing glands. This inflammation decreases the eyes' ability to produce natural tears, which help protect the eyes from irritation and keep them moisturized and lubricated. People who suffer from CDED often experience constant pain from eye irritation, including a sandy or gritty sensation that, if untreated, can lead to scarring or ulceration of the cornea, which can lead to a partial or total loss of vision.

Most cases of CDED result from normal aging of the eye; however, CDED or dry, irritated, tired eyes can occur at any age. It is estimated that nearly 75% of people over the age of 65 will experience CDED conditions. CDED occurs in both men and women; however, it is most common in women who are post-menopausal or pregnant. Approximately 4 million Americans, of which approximately 90% are women, have CDED as a consequence of Sjogren's syndrome, which is a chronic, slowly progressive autoimmune disease characterized by dryness of the eyes and mouth and recurrent salivary enlargement. Other diseases, such as rheumatoid arthritis, lupus, scleroderma, and thyroid disease, can also cause CDED. In addition, health, environmental, and lifestyle conditions can also cause CDED. For example, people suffering from allergies (approximately 50 million people) and people who wear contact lenses (approximately 38 million Americans), have a greater risk of developing CDED. Other circumstances that significantly dry, irritate, and fatigue the eye include: computer use; low humidity environments, such as flying in an airplane, in which the relative humidity is typically between 5% to 15%; certain medications; eye surgery; and certain medical conditions, such as bletharitis (inflammation of the eyelids).

Some early signs of CDED include: 1) an occasional burning sensation in the eyes when a person is in an area of low humidity or high pollution; 2) a persistent and painful gritty sensation in the eyes; 3) an inability to cry under emotional stress; 4) decreased tolerance of contact lenses; and 5) in extreme cases, unusual sensitivity to light, severe eye pain, or diminished vision. In the early stages of the disorder, these symptoms may come and go, but become more persistent as the condition worsens. For most CDED cases, patients experience a greater discomfort as the day-progresses.

Over 25,000 people a day turn 50 years old in the U.S. alone. It is estimated that by 2010, over 140,000,000 Americans will be over the age of 50. As mentioned above, if dry eye conditions are left untreated a person may develop CDED and, eventually, a loss of vision. Thus, with a significant portion of the population aging, the incidence of dry eyes will increase significantly, as will the risk of developing CDED.

The hydration process of eyes and, in particular, the corneal epithelium, includes tear production, evaporation, and outflow loss. Indeed, studies suggest that dry eye conditions are associated with an increased evaporation of tears from the ocular surface. Further, increased humidity around the eye significantly reduces, if not stops, the evaporation of tears and can restore and thicken the lipid layer. See William D. Mathers, M. D., et al., "Tear Flow and Evaporation in Patients with and without Dry Eye", Ophthalmology, Vol. 103, no. 4 (April 1996), pp. 664-669; William D. Mathers, M. D., "Ocular Evaporation in Meibomian Gland Dysfunction and Dry Eye", Ophthalmology, Vol. 100, no. 3 (March 1993), pp. 347-351; Donald R. Korb, O. D., et al., "Effect of Periocular Humidity on the Tear Film Lipid Layer", Cornea, Vol. 15, no. 2 (1996), pp. 129-134.

Presently there is no cure for CDED; however, there exist various treatments that are designed to alleviate the often debilitating pain and discomfort caused by dry eye conditions. Such treatments include artificial tear solutions, moisture chamber glasses, and punctal occlusion.

The most common treatment for people with dry, irritated, or tired eyes is artificial tear solutions, both prescription and over-the-counter eye drops. Artificial tear solutions may or may not contain preservatives. The preservatives used in artificial tear solutions have little or no toxicity; however, artificial tear solutions with preservatives can cause irritation if used frequently. In fact, artificial tear solutions with preservatives are not recommended for frequent use. CDED patients typically need to frequently apply artificial tears, which prohibits the use of artificial tears with preservatives. Preservative-free solutions are available; however, they are expensive and prone to bacterial contamination. While artificial tears primarily increase the comfort of people suffering from dry, irritated eyes, when used frequently they may rinse away the natural tears necessary to reestablish a normal tear film. Frequent use of artificial tears is also expensive; individuals suffering from CDED can spend approximately $300 a year on artificial tears.

Another treatment for dry, irritated eyes is ointments. Typically used for nighttime relief, ointments often blur vision, are messy, awkward to apply, and often do not provide an effective treatment.

Another treatment includes the use of moisture chamber glasses. Moisture chamber glasses are custom-made products designed to alleviate the pain and discomfort caused by dry eye conditions. There are no commercially available moisture chamber glasses; they must be custom fit by an optician and can be prohibitively expensive for the average consumer. Studies have suggested that conventional swim goggles may also be helpful in preserving moisture in dry eyes, as well as protecting eyes from exposure to air currents, such as air conditioning and wind gusts. See, e.g., Donald R. Korb, O. D., et al., "Effect of Periocular Humidity on the Tear Film Lipid Layer", Cornea, Vol. 15, no. 2 (1996), pp. 129-134. However, conventional swim goggles are not designed for prolonged use and can be uncomfortable to the wearer. Although conventional swim goggles are well designed for the intended use of swimming, the application of conventional swim goggles as a moisture chamber has numerous drawbacks, including: 1) the optics and field of view are designed for swimming; 2) conventional swim goggles typically have a narrow orbital seal that is designed to keep water out and which is located inside the orbital bone and supported by the sensitive inner ocular area; 3) the straps are designed for short-term wear, under tension, and are not designed for sleeping; 4) the lens and body design is manufactured of a polycarbonate rigid plastic, which is inherently uncomfortable because of its rigid nature and because the exterior contour creates pressure on the eye socket when the wearer is laying down; 5) conventional swim goggles encompass a smaller surface area around the eye, thereby reducing the potential to trap moisture and heat from the skin surrounding the eye; 6) conventional swim goggle designs tend to cut off capillary blood vessels of the skin in the area surrounding the eyes; 7) conventional swim goggle lenses are typically treated with an anti-fog coating, which is either hydrophobic, hydrophilic, or a blend of the two, and which can cause irritation to the eyes.

Punctal occlusion, the closure of the tear ducts, is another type of treatment for dry eyes that can provide an increased volume of tears remaining in the eye area by decreasing drainage. Under this method of treatment, the lower puncta, which carry away the majority of tears, are sealed using a collagen or silicone plug, or by surgery, via electrocautery or an argon laser. Plugging is typically done for evaluation purposes or when the sufferer's dry eye conditions vary in severity. A collagen plug lasts only a short time, may not occlude completely, and is eventually absorbed. The silicone plug is not absorbed, but can easily be removed. Surgical occlusion is a permanent treatment option for dry eye sufferers; however, surgery may have to be repeated because the puncta tend to reopen. Punctal occlusion can be an expensive treatment for dry eye conditions, ranging in price from $500 to $650.

Thus, a need exists for an apparatus, system and method for treating dry eye and/or irritated eye conditions that is natural, easy to use, comfortable and safe to the wearer, inexpensive, and which provides therapeutic benefits for the eyes without the discomfort, invasiveness, and limited use of the currently available treatments. A need also exists for an apparatus, system and method that can be used to promote healthy eyes and can reduce the possibility of developing CDED by improving the health of the lipid layer. Further, there is an unmet need for such an apparatus and method that allows for removably engageable components to facilitate customization of moisture and/or medicinal treatment, sanitary use by one or multiple users, and communication of moisture and/or medicine to each respective eye of the user.

SUMMARY OF THE INVENTION

Generally speaking, the present invention is directed towards an apparatus, system and method for treating dry eye and/or irritated eye conditions and which helps control, maintain and/or increase the temperature and humidity around the eyes to aid in limiting evaporation of natural and/or artificial tears. The present invention is also directed towards an apparatus, system and method for promoting healthy eyes by aiding in thickening the lipid layer. The present invention is also directed towards an apparatus, system and method that provides for controlled application of medicine to the eyes. Further, the present invention provides for communication of moisture and/or medicine to the eyes through the provision of removably engageable moisture pads which position an ocular cavity in communication with the eye where moisture and/or medicine can be communicated to the eye surface.

The apparatus of the present invention comprises two soft, pliable eyecups that each include a curved lens and contoured frame. The eyecups are connected by a soft, pliable bridge. The soft lenses of the present invention are maintained within the soft contoured frame, which is designed and constructed to encircle the orbital bones of the eye sockets, creating a custom, comfortable fit and effective seal over each eye. In a preferred embodiment, attached to each frame is a gasket that further aids in sealing the apparatus over the eyes and which provides additional comfort to the wearer. A contoured strap, which is attached to the eyecups, maintains the proper positioning of the apparatus on the wearer. Further, in a particularly preferred mode of the device, interior sidewalls of each eyecup are adapted to engage with removably engageable moisture pads having ocular apertures therein to form individual respective ocular cavities immediately adjacent to the respective eye surface when in use.

The present invention is also directed to a system comprising the apparatus described above used in conjunction with a moisture pad. The moisture pad can be inserted in removable engagement with an interior sidewall of the apparatus and having an ocular cavity which surrounds the eyes of the wearer to provide further aid in treating dry eye and/or irritated eye conditions. The moisture pads can be moistened, moistened and heated, or moistened and cooled to further aid in alleviating dry eye and/or irritated eye conditions. The moisture pads can also be provided in moisture tight packaging for mobile use or replenishment of the device during elongated use.

In a particularly preferred mode of the device, the moisture pads are removably engageable within the eyecups through biased outward force of the perimeter of each moisture pad upon the sidewall of the interior cavity of each eyecup. Each moisture pad can be prepackaged for sterility and pre-moistened with water or other moistening fluids. Such disposable prepackaged moisture pads would allow for customization of treatment for each user and replenishment of the moisture or medicinal treatment to the eyes by replacement of the moisture pads. Further, by engaging the moisture pads at their perimeter edge, in a biased engagement to the sidewall of each eye cavity, replenishment of moisture to the pads can be accomplished through channels formed through the sidewall to the exterior of the device.

Accordingly, it is an object of the invention to provide an apparatus and system, and methods for using such an apparatus and system, to provide an improved treatment for sufferers of dry eyes, dry eye syndrome, CDED, and irritated eyes that is simple and comfortable.

Another object of this invention is to provide an apparatus and system, and methods for using such an apparatus and system, to provide improved treatment for sufferers of dry eyes, dry eye syndrome, CDED, and irritated eyes that can be used for immediate and long-lasting relief.

A further object of this invention is to provide an apparatus and system, and methods for using such an apparatus and system, that improves quality of rest or sleep and reduces the need for other dry eye treatments, such as artificial solutions and ointments.

Still another object of this invention is to provide an apparatus and system, and methods for using such an apparatus and system, that improves comfort during air travel.

Still another object of this invention is to provide an apparatus and system, and methods for using such an apparatus and system, that creates a moisture retaining chamber around each eye, which promotes the health of the eyes while at the same time preventing and/or inhibiting the development of severe dry eyes.

Still another object of this invention is to provide an apparatus and system, and methods for using such an apparatus and system, that can alleviate, reduce, and/or prevent dry eye syndrome and/or CDED.

Still another object of this invention is to provide an apparatus and system, and methods for using such an apparatus and system, that increases hydration of the eyes.

Still another object of this invention is to provide an apparatus and system, and methods for using such an apparatus and system, that can promote healthy eyes.

Still another object of this invention is to provide an apparatus and system, and methods for using such an apparatus and system, that aids in the application of particular medicines.

Yet another object of this invention is the provision of such a device that also allows for easy customization of treatment by employing removably engageable moisture pads.

A still further object of this invention is the provision of such an apparatus and method that employs such moisture pads in a removable engagement that allows for exterior replenishment of the moisture content of the pads.

The invention accordingly comprises the features of construction, combination of elements, and arrangement of parts which will be exemplified by the constructions hereinafter set forth, and the scope of the invention will be indicated in the claims.

BRIEF DESCRIPTION OF THE DRAWING FIGURES

In the drawing figures, which are not to scale, and which are merely illustrative and wherein like reference characters denote similar elements throughout the several views:

FIG. 11 depicts another mode of the device which employs moisture pads which removably engage with the sidewall of the cavities formed by the eyecups.

FIG. 12 shows a rear view of FIG. 11 showing one moisture pad engaged within the eye cavity and one moisture pad poised for engagement.

FIG. 13 is a side view of a moisture pad enclosed in a sealed package.

FIG. 14 depicts a sectional view of an embodiment of the device featuring a moisture pad having a sloped exterior surface.

FIG. 15 is a sectional view of an embodiment of the device showing a moisture pad adapted for removable engagement with the eye cup having a lip that provides the gasket for engagement with the face of the user.

FIG. 16 depicts a sectional view of the moisture pad having a rear cavity adapted to engage a hot or cold temperature pack.

FIG. 17 shows a sectional view through a moisture pad having a rear pocket adapted to engage a hot or cold temperature pack opposite an ocular aperture for the eye.

DETAILED DESCRIPTION OF THE EXEMPLARY EMBODIMENTS

Figure 1:
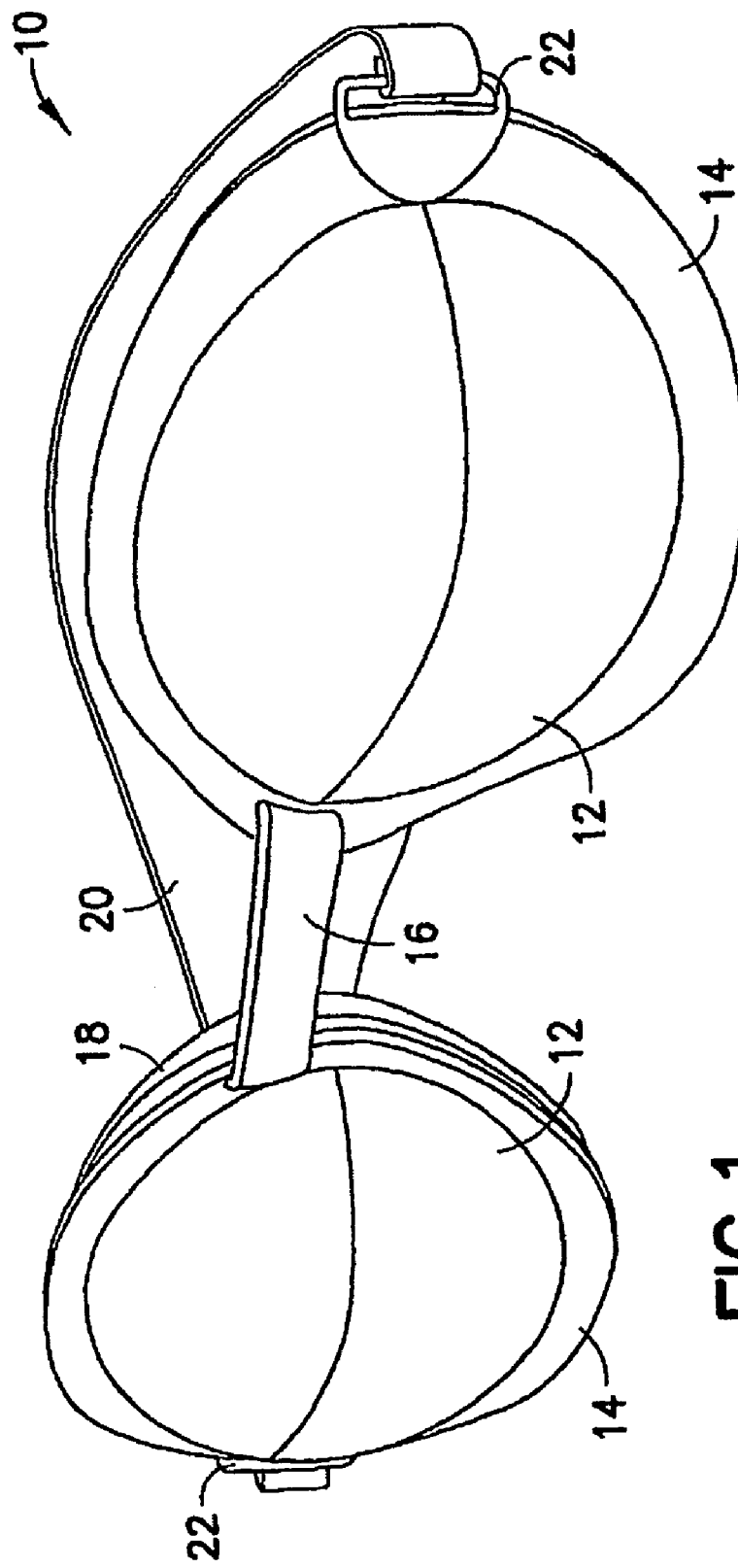
FIG. 1 is a front perspective view of an apparatus for treating dry eye conditions constructed in accordance with one aspect of the present invention.

Generally speaking, the present invention is directed towards an apparatus, system and method for treating dry eye and/or irritated eye conditions and which helps control, maintain and/or increase the temperature and humidity around the eyes to aid in limiting evaporation of natural and/or artificial tears. The present invention is also directed towards an apparatus, system and method for promoting healthy eyes by aiding in thickening the lipid layer. The present invention is also directed towards an apparatus, system and method that provides for controlled application of medicine.

In developing the apparatus, system and method of the present invention, the following information and design characteristics were taken into consideration:

Description of the Orbits from *Gray's Anatomy:* "The orbits are two quadrilateral, pyramidal cavities, situated at the upper and anterior part of the face, their bases directed forward and outward, and their apices backward and inward so the axes of the two, if continued backward, would meet over the body of the sphenoid bone. Each orbit is formed of seven bones, i.e., frontal, sphenoid, ethmoid, superior maxillary, malar, lachrymal, and palate, three of which are shared by both orbits, i.e., the frontal, ethmoid, and sphenoid".

Anatomical Considerations in the Design of the Invention: The design of the present invention takes into account the shape and contour of the bones of the face and the orbit region and uses this structure as support for the apparatus. Specifically, the frontal (supra-orbital ridge), superior maxillary, malar, and nasal bones were considered when determining the shape and contour of the apparatus. Due to ethnic variation, size, and gender, an optimized profile was determined that minimizes the pressure points on critical areas of this sensitive area. The present invention also is designed to minimize tissue pressure and occlusion of various vessels and nerves in the area of contact. Specifically, the present invention utilizes the bone structure for support and relies upon the muscle structure of the orbit area as additional protection of the arteries, veins, lymph vessels, and nerves.

Muscle Structure Considerations in the Design of the Invention: The apparatus of the present invention mimics the contour and general shape of the orbicularis palpebrarum, also referred to as the orbicularis oculi muscle, muscle structure. The frontalis portion of the occipito-frontalis muscle, the continuation of the pyramidalis nasi, and the corruggator supercilii, further protect the upper and nasal portions of the contact area.

Nerve Considerations in the Design of the Invention: The facial nerve divides in front of the ear into six branches that serve the scalp, forehead, eyelids, muscles of facial expression, cheeks, and jaw. The design of the present invention avoids the main trunk and minimizes pressure points on these nerves when the invention is worn, or if the patient were to lie on a pillow placing extra pressure on this area during sleep.

Blood Vessel Considerations in the Design of the Invention: The angular artery, orbital artery, and branches of the anterior temporal artery anastomose with the infra-orbital, and after supplying the lachrymal sac and orbicularis palpebrarum muscle, terminate by anastomosing with the nasal branch of the ophthalmic artery. Closing off the blood supply, or reducing the anastomosing, reduces blood flow in the area. Blood flow is further reduced if the capillaries are compressed by producing a design that compromises these delicate structures.

Primarily, the frontal vein and the communicating branch with the ophthalmic vein were considered in the shaping of the present invention in the nasal area. The nasal arch vein is avoided by the clearance provided by a flexible nose bridge. As the frontal vein moves down the face alongside the inner nasal, the present invention also avoids pressuring the angular vein.

The important anastomosis of the angular vein and the sinus is associated with proper circulation and is within the contact area of the invention. Thus, the present invention design in the described areas was modified to optimize fit and minimize the occlusion of these important veins. The health and well-being of the vein structures around the eye are associated with visual beauty in modern society; therefore, it is important in the design of the present invention to maximize health and beauty aspects of the invention, thus, occlusion of the veins should be avoided.

Lymphatic Vessels in the Orbital Area: Superficial lymphatic vessels of the face are numerous and generally accompany the frontal vessels in the area of the orbits. Compression of the superficial lymphatic vessels is minimized by the minimal localized pressure exerted by the apparatus of the present invention.

Fitting the greatest range of face sizes, ages, bone structures, and accommodating sensitive skin, determined the combination of materials of the present invention. Raw anthropomorphic data was utilized from ANSI Z87.1 1989, Alderson Head Form data and percentiles, and from The Measure of Man & Woman: Human Factors in Design, Revised Edition, by Alvin R. Tilley and Stephen B. Wilcox, December 2001.

Application and intended use were other factors taken into consideration for the design of the present invention, namely, when and how to use a dry eye treatment to derive the greatest therapeutic benefits. The present invention is designed for use when resting or sleeping. The design of the apparatus and system of the present invention prevents a sufferer of dry eye conditions from inadvertently touching or rubbing the eyes during the night, which can be a significant problem after many types of eye surgery. Also, incomplete closure of the eyelids while sleeping causes excessive drying of the eye that may cause significant damage to the cornea. These problems can be avoided if the present invention is utilized at night. As such, the present invention can improve the quality of sleep, support post-eye surgery healing, and aid in the acceleration of healing due to the improved conditions when the present invention is worn.

Taking into account all of the above design considerations, the apparatus of the present invention comprises two soft eyecups, that each include a soft lens and a soft frame, and which are connected by a soft, pliable bridge. The lenses, which are curved, and the frames are each made of a soft, pliable material. The lenses are maintained within a soft, pliable, and contoured frame that is designed and constructed to encircle the orbital bone of the eye sockets, creating a custom, comfortable fit and effective seal over each eye. In a preferred embodiment, attached to each frame is a gasket that further aids in sealing the apparatus over the eyes and which provides additional comfort to the wearer. A contoured strap, which is attached to each frame, helps maintain the proper positioning of the apparatus on the wearer.

Referring now to FIGS. 1 through 5, the apparatus for treating dry eyes and irritated eyes, generally indicated as apparatus 10, has curved lenses, generally indicated as 12, which may be either translucent, opaque, transparent, and/or of optical quality in order to provide maximum comfort to the wearer. Lenses 12 are coupled to frames, generally indicated as 14, which together make up the eyecup and which are connected to a second eyecup by a bridge, generally indicated as 16. A gasket, generally indicated as 18, is coupled to each frame 14. A strap, generally indicated as 20, is affixed to frames 14 via fasteners 22 to maintain apparatus 10 on the wearer. The apparatus of the present invention, when constructed of the appropriate materials and used as described herein, helps maintain and/or increase the humidity within the apparatus thus aiding in alleviating, treating, preventing and/or reducing the effects of dry eye syndrome and CDED.

The lenses and the frames are designed and constructed to balance the planned material, primary physical properties of Flex Modulus, 6000 psi and ASTM D790, Durometer Hardness, a scale "90" ASTM D2240, and Compression Set, 20% ASTM D395 73.degree. F., 22 hr., with the mechanical shape and how it is influenced by these factors. Anthropomorphic data was applied in the design and ranges of fit were established for the area around the less sensitive occipital bones. This area varies within the established ranges, and to make the apparatus as comfortable as possible, the apparatus self-conforms and seals this area for moisture retention. Comfort is a primary concern and established comfort criteria include reduction of pressure points in the contact area. The design of the apparatus of the present invention also takes into consideration that the patient may create additional pressure loading on the mechanism by lying on the pillow face down or turning during the night.

The eyecup is functionally unique in that the hemispherical lens provides a resilient support mechanism for the flowing anthropomorphic frame area. On any point of the frame area the anthropomorphic shape is designed to flex, follow, and move as needed by the individual's unique facial contour. Additionally, if the pressure on the gasket, which will be described in greater detail below, exceeds the limit of comfortable compression, the frame will then accommodate the pressure maintaining the seal and comfort. The actual flexibility of the invention is primarily achieved by the combination of the flexural modulus of the material and engineered shaping of the hemispherical area and frame. The variable part thickness also influences the final performance and characteristics to create the unique attributes described for this invention. Commonly, products for the eye protection industry are manufactured with a hemispherical rigid lens and a frame based on simple geometric shapes. These rigid materials and non-specific designs are ineffective at sealing the complex area of the occipital bone structure or providing the comfort required for people who need to use this type of product.

The eyecup, including a lens and frame, and the bridge of the present invention can be manufactured using a thermoplastic, including, but not limited to: ABS (Acrylonitrile Butadiene Styrene), Acetal (POM)-(Acetal (polyacetal)), Acrylic (Acrylic), Acrylic (PMMA)-(Polymethyl Methacrylate), Acrylic (SMMA)-(Styrene Methyl Methacrylate Copolymer), Cellulose Acetate, Cellulose Acetate Butyrate, Ethylene Vinyl Acetate, HDPE (polyethylene, high density), HIPS (polystyrene, high impact), Ionomer, LPDE (polyethylene, low density), MDPE (polyethylene, medium density), Nylon (Polyamide-nylon), PBT (Polybutylene Terephthalate), PC (polycarbonate), PCT (Polycyclohexylene Terephthalate), PCTG (Polycyclohexylene Dimethylene Terephthalate), Polyethylene, PET (Polyethylene Terephthalate), PETG (Polyethylene Terephthalate Glycol Comonomer), PP (Polypropylene), PPO (Polyphenylene Oxide), PS (Polystyrene), PUR (Polyurethane), PVC (Polyvinyl Chloride), PVC+PUR (Polyvinyl Chloride+Polyrurethane Alloy), Polyester TP (Polyester, thermoplastic), Polyester TS (Polyester Thermoset), SAN (Styrene Acrylonitrile), SB (Styrene Butadiene Block Copolymer), SBS (Styrene Butadiene Styrene Block), SEBS (Styrene Ethylene Butylene Styrene Block Copolymer), SIS (Styrene Isoprene Styrene Block Copolymer), TPE (Thermoplastic Elastomer), TPO—(Thermoplastic Olefin Elastomer), TPU (Polyurethane, Thermoplastic Elastomer-TPE).

The following thermoset materials, which have similar properties, are also appropriate for application to the present invention: silicone, Rubber, neoprene, Buna-N (nitrile) Rubber, Butyl Rubber, EPDM (ethylene-propylenediene methylene), SBR rubber (styrene butadiene), Epichlorohydrin Sponge Rubber, Gum Rubber, Hypalon Rubber, Latex (Natural Rubber), Neoprene Rubber, Polyurethane Rubber, and any other thermoset not listed but with properties appropriate for application to this invention.

Additionally, the eyecup and the bridge could be manufactured from a flexible cellular material, including, but not limited to: Polyurethane ether based foam, Polyurethane ester based foam, Polyethylene foam, Polyethylene crosslinked foam, Ethylene Vinyl Acetate foam, Silicone foam, PVC (Polyvinyl Chloride) foam, Polyimide foam, Ionomer foam, and any other flexible cellular material.

Alternatively, in addition to the thermoplastic and thermoset materials, the eyecup and the bridge can be manufactured using a gel, fluid, or particle-filled structure.

There are any number of ways of manufacturing the eyecup and the bridge of the present invention, including, but not limited to: injection molding, compression molding, vacuum forming, pressure forming, mechanical forming, casting, hot sealing, sonic welding, or other methods used in the fabrications of the above listed materials.

Lenses 12, depicted in FIGS. 1 through 7, are curved from a circumferential edge 13 to create a humidity or interior chamber above and around the wearer's eyes. In a preferred embodiment, lenses 12 have an eight-base curvature to allow for blinking. Lenses 12 are made of a soft, pliable material, such as silicone or flexible polyurethane, or any one of the materials listed above, and can be translucent, opaque, transparent, and/or of optical quality to provide maximum comfort to the wearer. In a preferred embodiment, lenses 12 are formed of flexible polyurethane. Lenses 12 can also be colored to promote additional therapeutic benefits such as light and/or color therapy.

Lenses 12 can be either permanently affixed to frames 14, or may be removably mounted or maintained within frames 14 in a manner known in the art. For example, lenses 12 can be constructed to snap into a groove (not shown) located in the inner perimeter of frames 14. In an alternate embodiment, the frames and lenses can be formed of a single unitary piece. The lenses 12 so engaged form an interior cavity 27 defined by the lens 12, and the sidewall 29 of the interior cavity 27 where it meets with the aperture formed in the circumferential edge 13 of the lens 12. The lenses 12 might also be extruded in a unitary structure with the frames 14 in some embodiments wherein the frame 14 would be a bend in the circumferential edge 13 of the lens 12.

Frames 14 also are made of a soft, pliable material, such as silicone or flexible polyurethane, or any one of the materials listed above, and are preferably contoured to conform to the orbital bone around the eye socket to provide a snug, comfortable, and effective fit for the wearer. Bridge 16 connects frames 14 and can be adjustable to provide a custom, comfortable fit for the wearer. Bridge 16 is also constructed of a soft, pliable material such as flexible polyurethane. In an alternate embodiment, the frames, lenses, and bridge can be formed of a single unitary piece.

Figure 6:
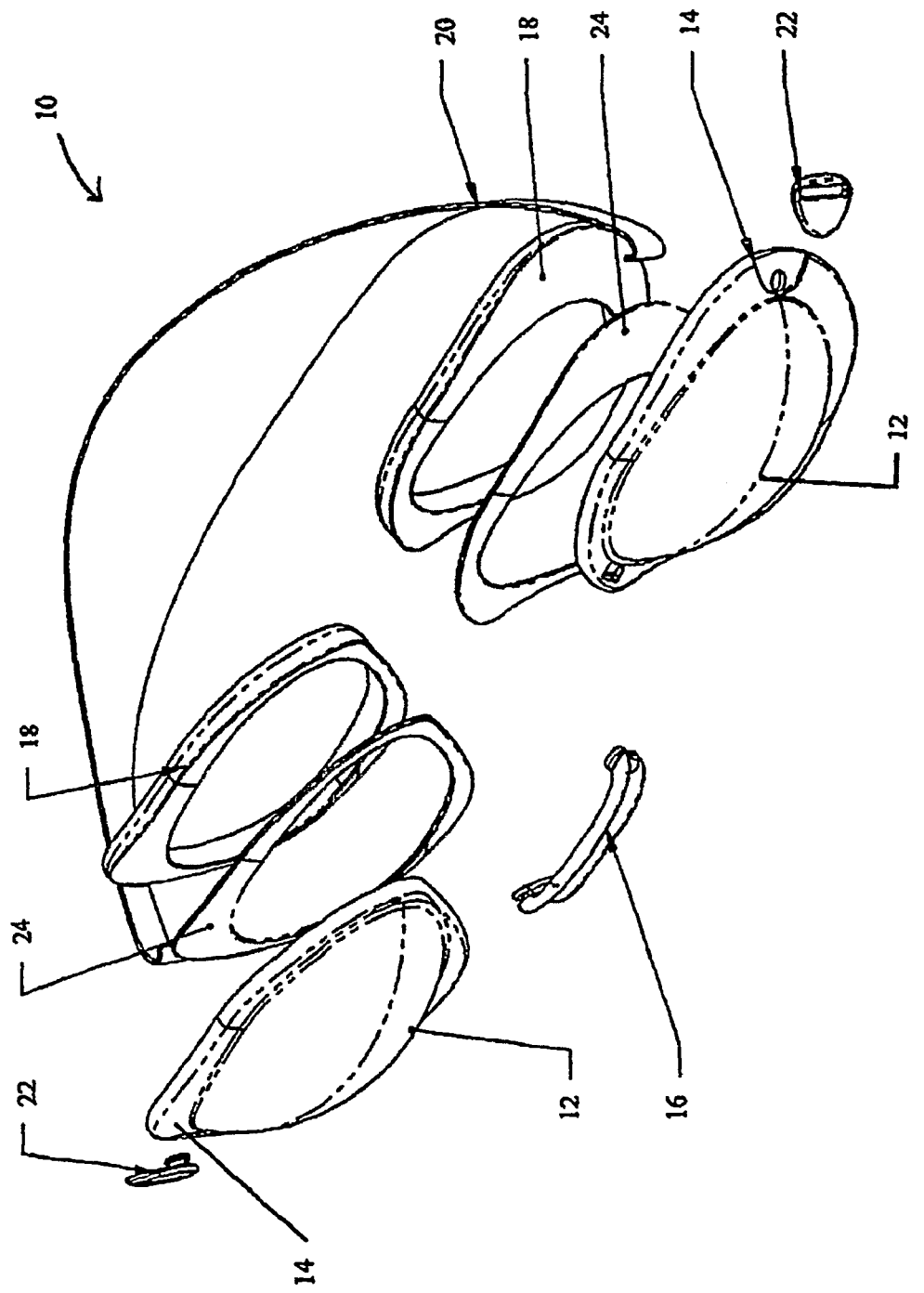
FIG. 6 is a detailed exploded front view of an apparatus for treating dry eye conditions constructed in accordance with one aspect of the present invention.
Figure 7:
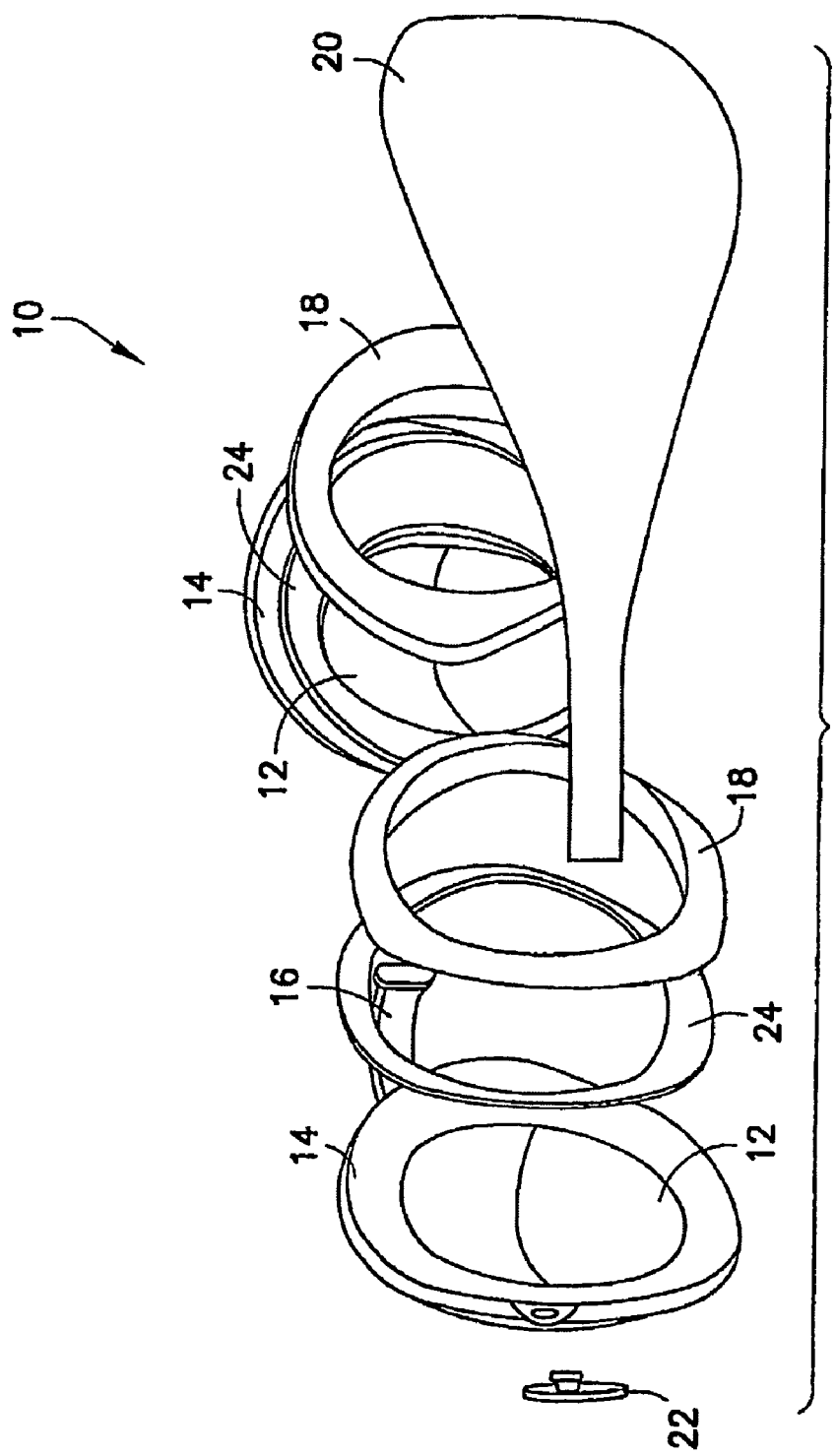
FIG. 7 is a detailed exploded back view of an apparatus for treating dry eye conditions constructed in accordance with one aspect of the present invention.

Gasket 18, as depicted in FIGS. 1 through 2 and 4 through 7, and FIGS. 11 and 12, can be coupled to frames 14 or to the rear surface of the lens 12 around the circumferential edge of the lens 12 if no frame is employed and the lens 12 is formed to provide the frame support. This will provide additional comfort to the wearer and to also provide a more effective seal around the eye sockets. In one embodiment, gasket 18 is permanently affixed to frames 14. In an alternate embodiment, gasket 18 can be removable from frames 14. For example, as shown in FIGS. 6 and 7, apparatus 10 can further comprise an attaching mechanism, generally indicated as 24 which such a means of attachment, which is coupled to frames 14, to which gasket 18 can removably attach. The attaching mechanism 24 providing this means of attachment can also be formed integrally with frames 14 as a matter of application specific design choice. Although attaching mechanism 24 can take any number of forms and materials as known in the art to achieve its intended function, in one preferred embodiment, attaching mechanism 24 comprises a hook and loop fabric strip to facilitate easy and quick interchanging of gasket 18. To attach gasket 18 to attaching mechanism 24, gasket 18 can have a compatible attaching hook and loop fabric mating material affixed to one side. In such an embodiment the wearer can replace gasket 18 upon extended use or the like. Of course other means of attachment might be used as would occur to those skilled in the art including adhesive, no permanent adhesive, a mechanical engagement, or other means of engagement adapted to the purpose at hand. In the embodiments employing moisture pads 26, the gasket 18 may be formed as part of the moisture pad 26.

Gasket 18 can be formed of any type of material that will provide a comfortable fit for the wearer while at the same time meeting the functional requirements of the gasket, for example, foam or a thin silicone member. In a preferred embodiment, gasket 18 is made of a visco-elastic, thermalforming foam, such as the commercially-available foam supplied by PAC Foam Products Corporation in Costa Mesa, Calif. Such a foam gasket will conform to the wearer's orbital bone structure, especially when warmed by body heat, to thereby create a comfortable and effective seal around the eyes.

In the preferred embodiment, balancing Indention Force Deflection (IFD) @25%, IFD @65%, and specific pound density of the present invention, relieves pressure points along the orbital area. This balancing works in combination with the tension of strap 20 and the anthropomorphic design of the eyecup.

In an alternate embodiment, gasket 18 is integral with the eyecup. For example, gasket 18 may be an extension of the hemispherical section of the lens, a portion of the frame, or a structure that is emanating from any or all of these sections and, as such, gasket 18 can be formed of any one of the materials listed above for the eyecup. In this alternate embodiment, the desired balance between the IFD @25%, the IFD @65%, and the pound density can be achieved by, for example, the frame itself without the addition of a separate gasket 18.

In an alternate embodiment, gasket 18 is an inflated structure comprised of a bladder that surrounds the orbital area.

In an alternate embodiment, gasket 18 is a gel-, fluid-, or particle-filled structure that self-conforms to the orbital structure. Gasket 18, when a filled structure, can be heated or cooled to promote the therapeutic benefits of the present invention.

Strap 20 is preferably made of a soft, and flexible or elastic material and is coupled to frames 14, preferably at opposite outer sides of frames 14. In the embodiment depicted in FIGS. 1 through 7, strap 20 is coupled to fasteners 22, which can be made of a flexible polyurethane or any one of the materials listed above for use in the eyecup, and which are coupled to opposite outer sides of frames 14. The design of fasteners 22 permits the wearer to sleep with the apparatus and contact the pillow or bedding without unnecessary pressure points on the wearer. See para. 42, Nerve Considerations in the Design of the Invention. In an alternate embodiment, frames 14 include two parallel slits on opposite outer sides for affixing strap 20 to frames 14. Other means of attaching strap 20 to frames 14 are known in the art. Strap 20 can be both removable and adjustable.

Figure 2:
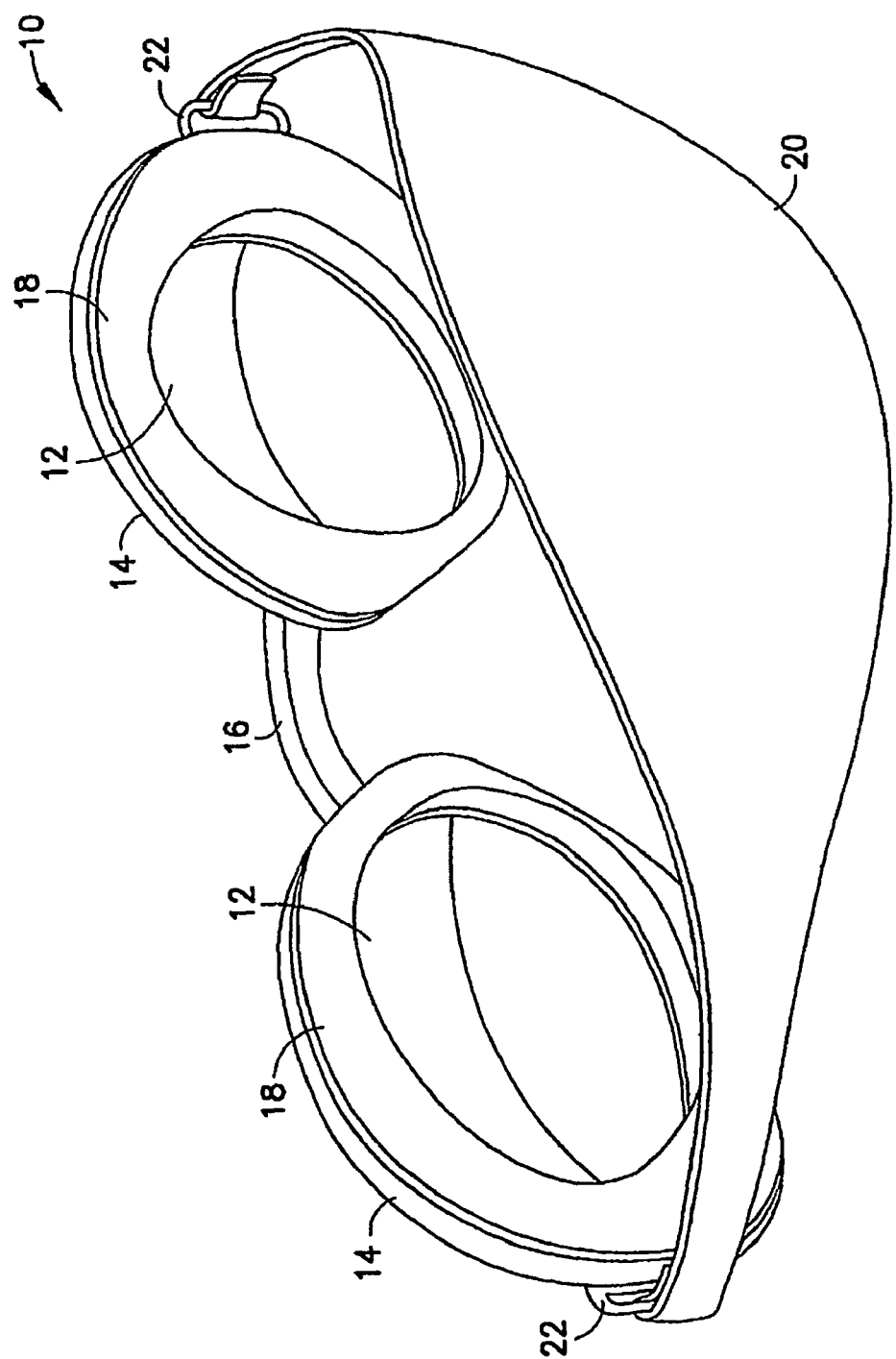
FIG. 2 is a back perspective view of an apparatus for treating dry eye conditions constructed in accordance with one aspect of the present invention.
Figure 3:
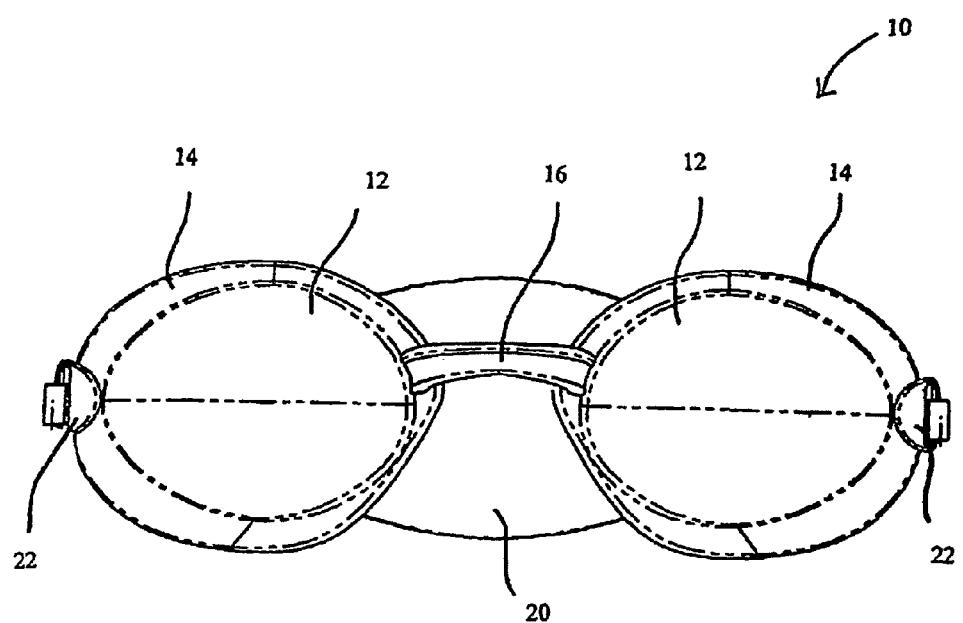
FIG. 3 is a front plan view of an apparatus for treating dry eye conditions constructed in accordance with one aspect of the present invention.

In a preferred embodiment, strap 20 is formed of an elastic material, such as a two-way stretch polyester blend, four-way stretch polyester blend, or cotton, polyester, and lycra blend materials, or any combination thereof, which aids in preventing snagging and pulling, thereby providing additional comfort to the wearer. In a preferred embodiment, strap 20 is shaped as shown in FIGS. 2 and 7, that is, strap 20 has a greater width at its mid-point, which further aids in holding the apparatus on the wearer and provides greater comfort to the wearer.

In a preferred embodiment, strap 20 is designed for low tension and maintains position of the apparatus with minimal interference to the capillary blood vessels of the skin and blood supply to glands and structure in the area surrounding the eyes. Additionally, the design of strap 20 minimizes the potential interference of the lachrymal glands and ducts. See paras. 39 and 40, Description of the Orbits from Gray's Anatomy and Anatomical Considerations in the Design of the Invention, respectively. This is achieved with a combination of the low-required strap tension and the rebound characteristics of the visco-elastic foam.

In the preferred embodiment, the "dynamic tension" which strap 20 and gasket 18 work together to achieve is the key to the long-term wearing comfort of the apparatus of the present invention. In the preferred embodiment, gasket 18 is made of a foam material that has an IFD @ 25% in a ratio to the strap tension and in combination with the pound density, although surface area of contact has a bearing on the comfort factors. The second measure of IFD is at 65%, which determines that the foam will not bottom out under normal strap tension, which brings into play the flexibility and design of the eyecup and its particular structural design.

The attachment mechanism of strap 20 can also include, but is not limited to: elastic head strap; synthetic and/or non-synthetic head strap; fabric head strap; stretch fabric head strap; designs that utilize the ear as the locator and support of any of the materials listed; designs that are open and woven in the fashion of a hair net; designs of a fabric, synthetic, non-synthetic, foam or plastic that encircle the head at or about the coronal line as defined by ANSI Z87.1-1989; designs that are adjustable or non-adjustable for straps, bands, or ear located attachments; designs that utilize snaps, Velcro.RTM., buttons, other standard fasteners or custom fasteners to attach strap 20 or that are used to adjust the tension or the combination of both; designs that utilize gravity, such as weighted fixtures that position and create the dynamic tension necessary to seal the unit to the orbital area, these would be used when a patient was being provided a spa facial and the head in a position to be conducive to dry eye therapy; designs that utilize an adhesive to attach the unit to the face, such as an adhesive that directly attaches to the eyecup and is located on the surface of the eyecup that comes into direct contact with the skin; methods such as placing the eyecup into position and taping the apparatus from the exterior, this type of application has particular value for juvenile patient applications or patients who may accidentally remove the apparatus or when critical cleanliness is required; or any combination of the attachment methods listed above can be used.

Figure 4:
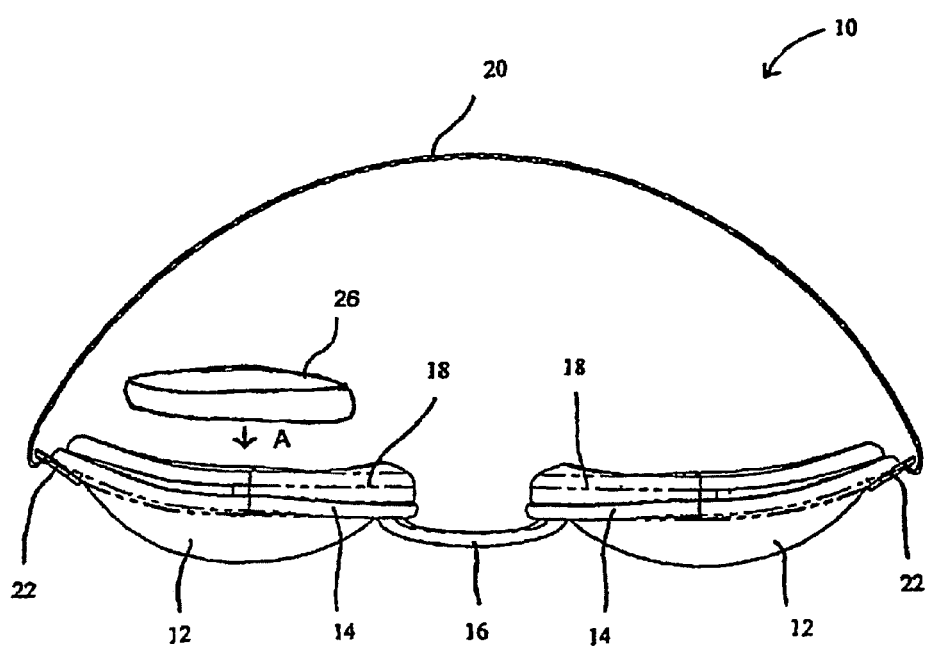
FIG. 4 is a top plan view of an apparatus for treating dry eye conditions constructed in accordance with one aspect of the present invention.
Figure 5:
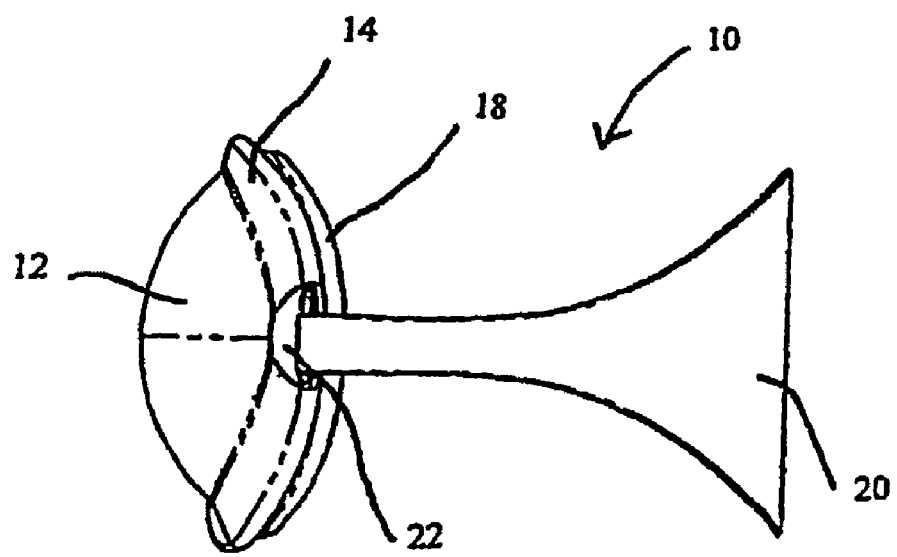
FIG. 5 is a side plan view of an apparatus for treating dry eye conditions constructed in accordance with one aspect of the present invention.

In another aspect of the present invention, in a system for treating dry eye and/or irritated eye conditions, shown in FIGS. 4, 11 and 12, the apparatus 10 further comprises a moisture pad, generally indicated as 26. As shown in FIG. 4, moisture pad 26 can be inserted between apparatus 10 and the eyes of the wearer in direction A. In a preferred embodiment, the moisture pads are made of viscous-elastic foam, which, when moistened, further help maintain, increase, and/or regulate the temperature and humidity within the chamber around the eye socket. The moisture pads can be moistened using water, artificial tears, or any other solution known in the art. In addition to being moistened, the moisture pads can be moistened and heated, or moistened and cooled, prior to being inserted into the cavity of lenses 12. The wearer can apply the apparatus including the moisture pads for a set amount of time, after which the wearer can remove the moisture pads and continue to wear the apparatus. The moisture pads, when used in combination with the apparatus of the present invention, can further increase and maintain the relative humidity within the chamber surrounding the eye socket for aiding in treating the effects of dry eyes, irritated eyes, and for promoting healthy eyes. Further, by employing a pair of eyecups 16, one for each eye, different treatments to each eye can be provided concurrently by employing moisture pads 26 soaked with differing liquids. For instance one with water for moisture and one with water and a medicine to treat only one eye in need of the medicine. This two-chamber construction provided by individual eyecups thus yields a superior system to a single eye chamber for both eyes.

In a particularly preferred embodiment of the device herein shown in FIGS. 11-17, the moisture pads 26 are adapted for removable engagement with the sidewall 29 of the interior cavity 27 adjacent to the lens 12. As shown in FIGS. 11 and 12, this preferred embodiment of the device which employs individual moisture pads 26 adapted to removably engage with the sidewall 27 of the interior cavities 27 of each eyecup 16 in a biased or other removable engagement therewith. Currently, it has been found that by forming the perimeter edge 31 of the moisture pads 26 slightly larger than the perimeter distance of the sidewall 29, that a biased engagement between the moisture pads 26 and the sidewall 29 can be achieved using foam or other materials adapted to absorb moisture and to resist compression. This provides an easy, yet secure mount of the moisture pads 26 once the user has compressed them slightly and then allowed them to spring back into a biased engagement with the sidewall 29. Since the moisture pads 26 are deformable to their mounting enclosure, one size or shape moisture pad 26 can fit a plurality of different shaped eye cups 16 so long as the perimeter edge 31 is equal too or slightly larger than the sidewall 29.

For an especially secure mount, as shown in FIG. 14, the perimeter edge 31 of the moisture pad 26 can be tapered as can the sidewall 29. The taper would place the narrowest portion of both the sidewall 29 and the perimeter edge 31, closest to the user's face. Once the user compresses the moisture pad 26 and allows its perimeter edge 31 to contact the sidewall 29, a biased engagement is formed by the outward bias of the moisture pad 26 and a means to hold the pad to the eyecup 16 and from falling out of its engagement therein is provided, since the pad is larger on the side placed adjacent to the lens 12 than that adjacent to the user's face.

All versions of the moisture pads 26 in this favored embodiment feature some form of an ocular aperture 33 formed in a center portion of the pad and having a dimension defined by an interior sidewall 35. The ocular aperture 33 can be a detent in one side surface as shown in FIG. 16, adapted to accommodate an eye of a user therein during use, or it may continue on in and axial communication through both sidewalls as in the other figures and communicate with the gap 15 behind it increasing the size of the treatment chamber for the user. Experimentation has shown moisture pads 26 which provide this ocular aperture 33 and engage with the sidewall 29 for the secure but removable mount, to be superior to other moisture pads because the ocular aperture 33 provides additional functional and operational benefits and the gap 15 can be employed for placement of temperature treatments or to increase the size of the chamber treating the eye depending on the components engaged along with the moisture pads 26.

Moisture pads 26 without the ocular aperture 33 in a loose mount or mount against the lens 12 have been found through experimentation to constrict the area provided for the user's eyes. With some users this may not be a problem but with many, this can be a very irritating problem, especially when the eye lashes hit the surface of the moisture pads 26 or even the surface of the eye itself can come into contact with moisture pads lacking the ocular aperture 33. Consequently, is has been found that employing the ocular aperture 33 with a passage or recess in the moisture pad 26 on the side contacting the user's face, provides great benefit in the use of the device and comfort of the user.

Additionally, engaging the perimeter 31 of the moisture pad 26 with the sidewall 29 places the moisture pad 26 and especially the formed ocular aperture 33, closer to the individual eye being treated during use thereby increasing effectiveness. In one preferred mode, a means to replenish the moisture pad 26 with liquid, without removing the device from the user's head is provided. The ocular aperture 33 is sized to accommodate the eyelashes and the eyelid and front of the eye therewithin thereby placing the eye to be treated in close proximity to the moisture pad 26. The interior sidewall 35 of the moisture pad 26 thus has a perimeter to provide the space necessary. As such, when the moisture pad 26 is compressibly engaged against the sidewall 29 as noted above, and the ocular aperture 33 is appropriately sized, an ocular aperture 33 is formed immediately adjacent to the eye which communicates moisture and/or medicine to the eye in close proximity thereby increasing transmission of moisture and/or medicine to the eye.

Additionally, if communication channels 37 can be formed through the individual eyecups 16 and communicate from the sidewall 29 to the exterior of the apparatus 16, wherein moisture or medicine can be easily communicated through the channels 37 and flow through the perimeter edge 31 of the moisture pad 26 and thereafter communicate to the ocular cavity 33 which as noted is placed immediately adjacent to the eye in this mode of engagement. If such replenishment is anticipated to occur frequently, or if transmission of moisture and/or medicine is to be limited to the ocular cavity 33, the exterior surface of one or both side surfaces 39 of the moisture pad 26 may be covered with a membrane that prevents passage of moisture. The provision of a surface which prevents moisture passage, thereby directs all of the moisture and/or medicine solely to the ocular cavity 33 where it would communicate through the porous interior sidewall 35. Additionally, because the device employs individual eyecups 16 with individual moisture pads 26 which form individual ocular cavities 33 around each respective eye, the type and amount of moisture or medicine communicated to each ocular cavity 33 through the channels 37 can be customized.

If replenishment is being provided through the channels 37, the compressed or outwardly biased mount of the perimeter edge 31 to the side sidewall 29, further facilitates passage of the moisture to the ocular cavity 33 between the sidewalls 39. Even without the sidewalls 39 present, it has been found that the biased engagement of the perimeter edge 31 of the moisture pads 26 to the sidewall 29 allows for superior communication of additional moisture or fluid from the channels 37 to the ocular cavity 33 and is also preferable due to the placement of the ocular cavity 33 closer to the eye while still providing a void to prevent contact with eye structures.

Moisture pad 26 and/or gasket 18 can be manufactured from materials including, but not limited to: visco-elastic polyurethane foam, hydrophilic polyurethane foam (e.g., Aquazone product by Foamex), polyurethane ether based foam, polyethylene foam, polyethylene cross-linked foam, ethylene vinyl acetate foam, silicone foam, PVC (Polyvinyl Chloride), Polyimide foam, Ionomer foam, Polyester based foam, latex foam, anti-microbial materials (e.g., anti-microbial foam or fabric), sponge (natural or synthetic), gauze, pulp, fiber, fabric (natural or synthetic), paper products, or any synthetic or natural material, which has the capacity to absorb and release moisture or other liquids.

Moisture pad 26 and/or gasket 18 can be made of a material listed above, and then covered, in whole or in part, in a fabric to further increase comfort to the wearer or add specific characteristics to the product.

In an alternate embodiment, the moisture pad can be used to administer medicine, for example, medicine can be infused into the moisture pad material and then delivered in a controlled manner. Specifically, medicines could evaporate, sublimate, or combine with the natural moisture present in the apparatus and be delivered to the eye. Moisture pad 26 can be used to administer medicinal eye drops by absorbing the medicinal eye drops. This type of administration would contain the medicinal eye drops in a superior manner by containing the medicine within the orbital area. Moisture pad 26 and/or gasket 18 also can be infused with an herbal treatment or a counter-irritant.

Still further, the especially preferred embodiments of FIGS. 11-17, allow for the use of prepackaged moisture pads 26 which can be sealed inside of a moisture retaining package 41. This allows the user great versatility in the use of the apparatus 10 as they can carry a supply of appropriately moistened or medicated moisture pads 26 on their person and easily engage them in the biased mount upon the sidewall 29 using any of the depicted engagements herein including slanted or straight, thereby positioning the ocular cavity 33 formed in each individual pad 26 in close proximity to their eye. Such proximity in an appropriately configured ocular cavity 33 is better able to avoid contact with the eye lashes, eye lid, and eye surface, than a solid pad engaged to the lens 12 or simply inserted in the cavity 27. Further, since the ocular cavity 33 is individually formed in each pad 26, each eye can be individually treated with different amounts of moisture, medicine, heat, cold, or other therapeutic treatment without regard to the other making the device highly customizable to the individual user's needs.

In the pre-packaged form shown in FIG. 13, versatility and ease of mounting by this embodiment of the pad allows the user to carry and easily use the device during travel on airplanes, in cars, or at home. Should their treatment involve prescription medication, the moisture pads 26 properly sized for the biased engagement against the sidewall 29 can be packaged in the sealed package 41 and dispensed from pharmacies or drug stores. In the event or a long trip or elongated treatment period, additional moisture pads 26 can be removed from the sealed package 41 and easily compressibly engaged to the sidewall 29. Should their treatment require more than one type of medicine or other moisture delivered treatment, different pre-packaged moisture pads 26 can be carried or purchased which will already be soaked in the appropriate solution and sealed in a package 41 for use as needed. Still further, the pads 26 themselves, can be heated or chilled while in the package 41 if temperature therapy is desirable to the user and since the two pads 26 are engaged in individual eyecups 17 and form separate treatment cavities around each respective eye, the treatment is exceedingly customizable.

In another aspect of the present invention, gasket 18 can be used for medicinal administration via skin contact. For example, hormone therapy, which is typically administered via a skin patch and which can be used to alleviate dry eye conditions, could be administered via gasket 18, which is in contact with the skin of the wearer when wearing the apparatus of the present invention.

In another aspect of the present invention, the current realization of the moisture pad places the surface away from the eye, actually allowing room for uninterrupted blinking action; however, the moisture pad can be designed and administered to apply controlled pressure onto the closed eye. The pressure would be controlled by factors previously described in measuring the thickness, IFD @25%, IFD @65%, and the density.

In another aspect of the present invention, moisture pad 26 and/or gasket 18 can be constructed of a material that has endothermic or exothermic properties. That is, moisture pad 26 and/or gasket 18 can be constructed of a material that automatically heats or cools the apparatus of the present invention and thereby improve eye comfort and health. For example, moisture pads 26 can be comprised of the same materials as used in hot packs, which are used for muscle comfort or warmth, such as for winter outdoor activities.

In another aspect of the present invention, the apparatus and system, including moisture pad 26 itself, can be heated or cooled to provide further comfort to the wearer. For example, the apparatus, along with moisture pad 26, could be placed in a microwave for a short period of time. Or as noted below, individual means for imparting heat or cold can be engaged within the eyecups 17 to or adjacent to the moisture pads 26 in the gap 15 formed between the perimeter mounted pad 26 and the eyecup 12. Since two separate moisture pads 26 are employed with two separate eyecups 12 one eye can be given a different temperature treatment than the other if the need arises just like the separate medicinal or moisture treatment. Because two eyecups 17 are used instead of a single cavity for both eyes, temperature and moisture treatment to each eye of the same user can be customized wherein a user could actually have one eye being heated while the other is exposed to cold.

Figure 8:
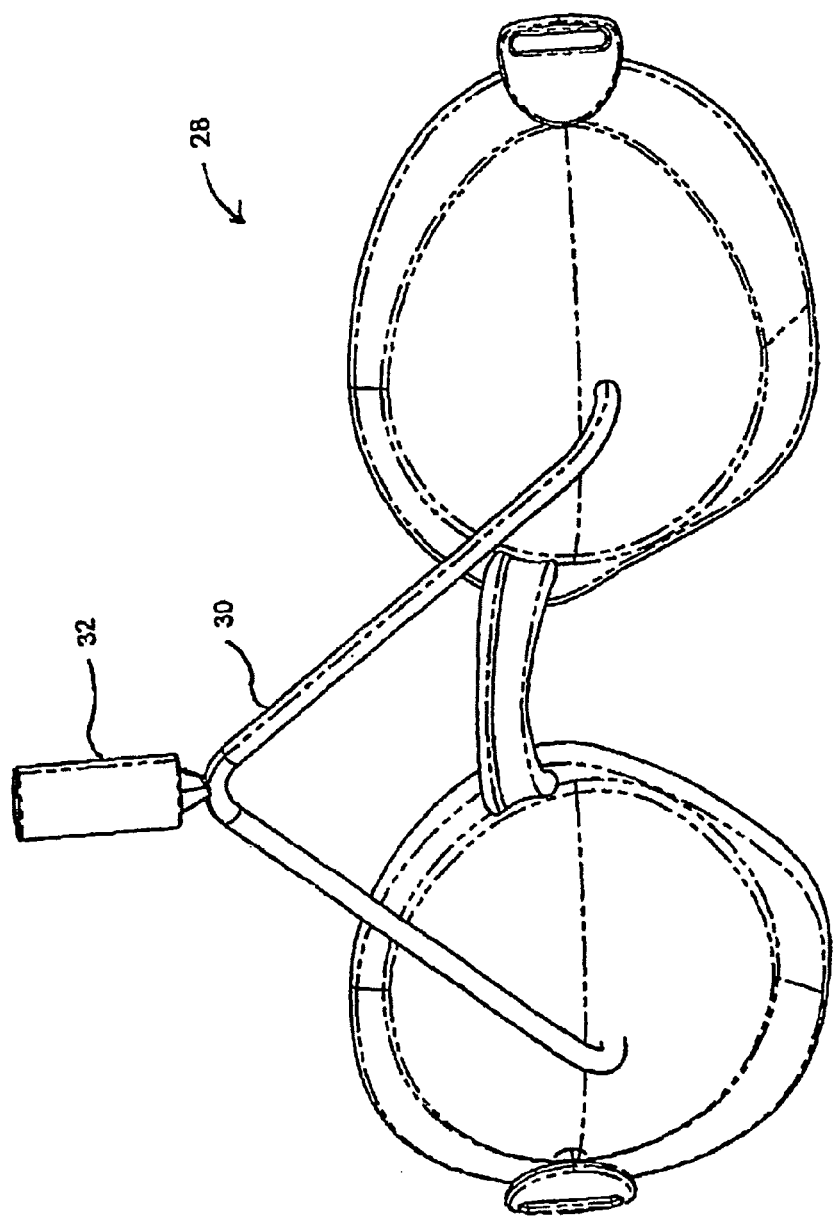
FIG. 8 is a front view of an alternate embodiment of an apparatus for treating dry eye conditions.
Figure 9:
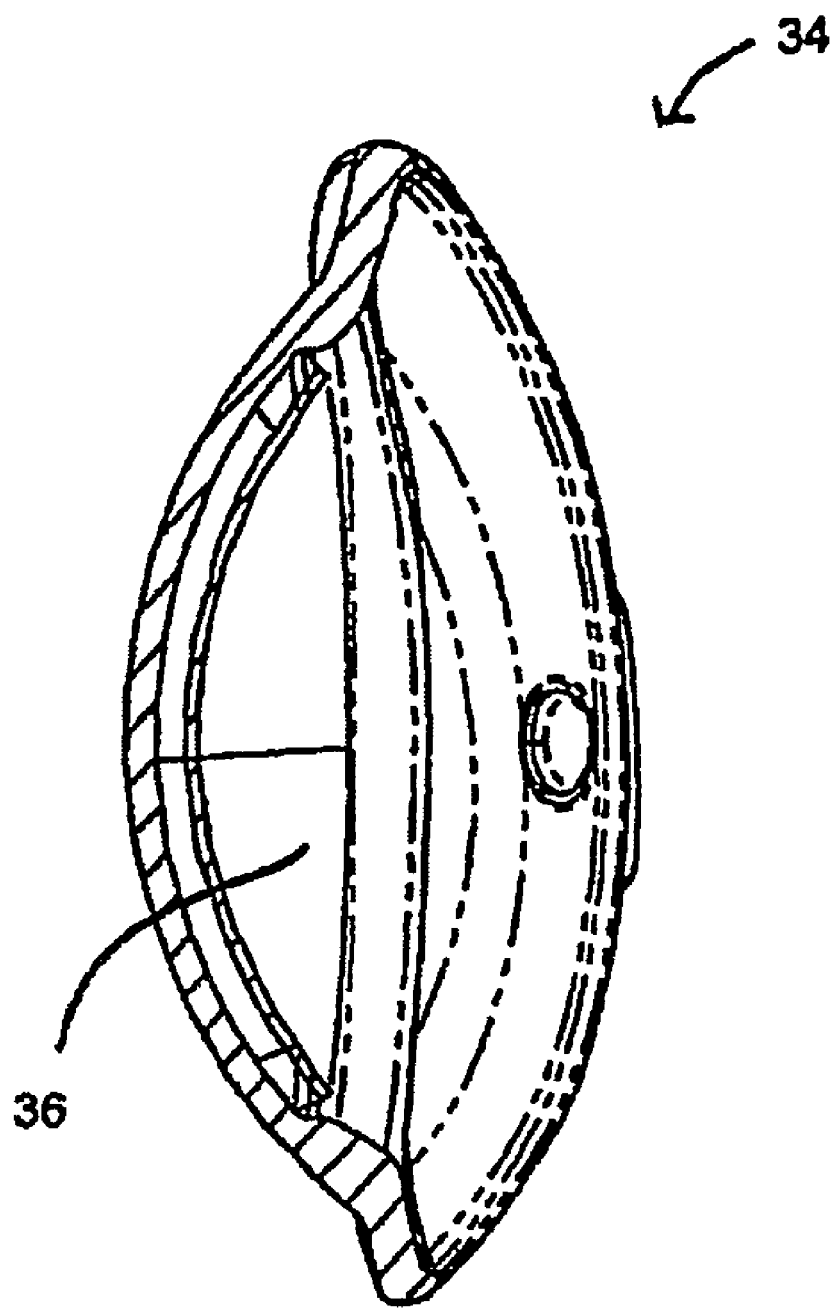
FIG. 9 is a side plan view of an alternate embodiment of an apparatus for treating dry eye conditions.

In alternate embodiments, shown in FIGS. 8 and 9, the apparatus of the present invention can be used to aid moisture delivery by adding moisture to lens within the eyecup 17 formed by the lens 12 and the gasket face. FIG. 8 depicts an alternate embodiment, generally indicated as 28, in which the delivery system that feeds the moisture into the eyecup 17 can be through a tube, generally indicated as 30, from a separate remote reservoir, generally indicated as 32. Alternately, FIG. 9 depicts an alternate embodiment in which the delivery system can feed moisture into the eyecup 17 by an internal reservoir system built into the eyecup 17, generally indicated as 34. For example, as shown in FIG. 9, the internal reservoir can be a pocket or a double lens design, generally indicated as 36, that is filled with moisture and is designed to slowly transfer into the chamber surrounding the eyes. This transfer of moisture into the orbital area can be by direct openings in the reservoir or membrane technology, such as a Gortex membrane, or wicking mechanism which utilizes a material to wick the moisture from the reservoir into the orbital area.

Figure 10:
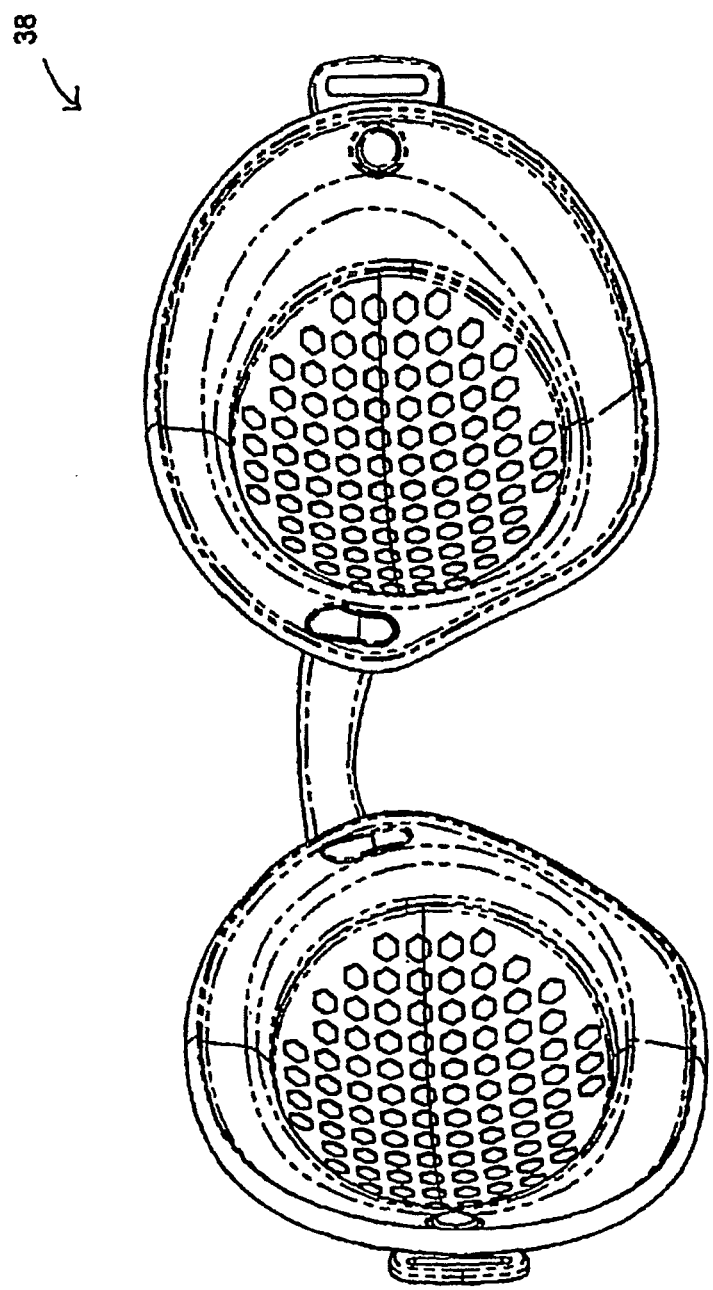
FIG. 10 is a back view of an alternate embodiment of an apparatus for treating dry eye conditions.

In another method for adding moisture to the eyecup 17, generally indicated as 38 in FIG. 10, the interior surface design of the eyecup 17 is molded with a textured pattern, for example, a shallow honeycomb design. This honeycomb texture can be sized to accept moisture into the pockets, yet the diameter would be small enough so that the meniscus of the liquid would retain the moisture rather than allowing the liquid to run out of the honeycomb pockets by gravity. This design can hold the pre-charge of moisture and create a large surface area for evaporation, thereby raising the relative humidity in each individual eyecup 17 without the addition of a moisture pad.

In another method for adding moisture to the eyecup 17, the interior surface of the eyecup 17 can be sprayed with water, artificial tear solution, spray eye mist, for example Biomist, or any other solution known in the art, before the wearer dons the apparatus of the present invention.

Shown in FIG. 15 is another preferred mode of the device shown as a sectional view of the moisture pad 26 adapted for removable engagement with a sidewall 29 adjacent to or in the eye cup having a lip 43 that provides the gasket 18 for engagement with the face of the user. This embodiment of the device would allow for a solid or harder frame 14 or unitary constructed frame 14 and eye cup 12 that might be more easily reusable since it could be more easily sterilized between uses. The lip 43 would provide the gasket 18 and padding to the user's face once the moisture pad 26 is operationally engaged in an as-worn position on the user. Of course the lip 43 shown in FIG. 15 might also be employed with the slanted perimeter edge 31 engagement of FIG. 14, for an especially secure mount of the moisture pad 26.

FIG. 16 depicts a sectional view of the moisture pad having a rear cavity 45 adapted to engage a means for communicating temperature change to the eye such as a hot or cold temperature pack 47 therein. Such a means to communicate heat or cold to the user's is best if it may be easily heated or chilled and is also adapted in size to be accommodated on the opposite side of the moisture pad 26 from the eye to protect the eye from direct temperature exposure. Currently envisioned components providing means to communicate temperature change to said ocular cavity include one or a combination of such from a group consisting of microwaveable or refrigerateable gel packs, stones and ceramics, chemically activated hot and cold packs, or the moisture pad itself being formed of material which may be heated or chilled. Other components that can be employed to provide either heat, or cold, to the eye of the user when engaged within one or both of the individual eyecups 17 as would occur to those skilled in the art are anticipated. Since each eye is surrounded by its own cavity and moisture pad 26, great customization is possible in the temperature and moisture therapy afforded to each individual eye.

This embodiment provides the ocular aperture 33 adjacent to the eye of the user, and providing the treatment cavity to communicate moisture or medicine from the pad 26 to the individual eye. It also allows for heat or cold to be imparted to the ocular aperture 33 from the temperature pack 47. The rear cavity 45 might also be formed in the moisture pad 26 as a pocket form as shown in FIG. 17 with a opening 49 providing access to the rear cavity 45. Further, the temperature pack 47 might also be engaged to the eyecup 17 and the moisture pad 26 inserted in-between the eyecup 17 and the eye since the moisture pad 26 engages the sidewall of the eyecup 16 rather that the interior surface. This engagement allows spacing between the interior of the lens 12 of the eyecup 17, to accommodate a temperature pack 47 if such a configuration is desirable and the temperature pack 47 could be engaged with releasable adhesive or frictional fit to the interior of the eyecup 17 or by simple containment between the interior of the lens 12 or other interior part of the eyecup 16 on one side, and the inserted moisture pad 26 on the other, using other means of removable engagement.

The pads 26 shown in FIGS. 16 and 17 could also have slanted perimeter edges 31 to fit the slanted sidewall 29 shown in FIG. 14 for a secure mount of the pads 26 in their individual eyecups 17. Because the slant makes the pad 26 wider at its rear, it remains removably engaged and this configuration could be used with any of the pads 26 herein with an eyecup 17 adapted to that engagement.

Data from tests of the apparatus and system of the present invention confirms the utility and efficacy of the invention. Specifically, testing confirms that use of the invention increases the temperature and relative humidity of the area surrounding the eyes, thereby reducing, and possibly preventing evaporation of natural and/or artificial tears, and/or preventing problems associated with increased evaporation, i.e., the dry eye conditions discussed above.

The results of testing the apparatus and system of the present invention on subjects without dry eye conditions are depicted in Table 1 below. For each test, temperature and humidity were measured over time, using a traceable hygrometer/thermometer, model no. 35519-020, calibrated to comply with ISO 17025. In Test 1 the subject wore the apparatus of the present invention for approximately 30 minutes during which the subject's eyes were closed 50% of the time and open 50% of the time. As Table 1 depicts, the temperature around the eyes increased 7.29% and the relative humidity increased by 52.29%. Use of the invention together with the moisture pads caused an even greater increase in temperature and relative humidity of the area surrounding the eyes. Notably, in Test 3 in which the subject wore the invention for ten minutes with the moisture pads and continued wearing the product for an additional forty-seven minutes, the temperature increased by 8.11% and the relative humidity increased by 83.90%. The other tests, which included varying the length of time the subject wore the invention with the moisture pads, and base line relative humidity in the room, also demonstrate increases in the temperature and relative humidity of the area surrounding the eyes.

TABLE 1

Testing of Apparatus on Subjects with Normal Eyes

| Time | Temperature | % Change from Base Temperature | Relative Humidity (RH) | % Change from Base RH | Comments |
|---|---|---|---|---|---|
| Test 1: Pleasanton, CA, Apr. 20, 2003 | | | | | |
| 7:44 PM | 73.5 | 2.04% | 41.47 | 13.33% | No moisture |
| 7:46 PM | 75 | 3.84% | 47 | 25.87% | added. |
| 7:50 PM | 76.32 | 5.44% | 52.2 | 34.77% | |
| 7:55 PM | 77.5 | 5.99% | 55.89 | 40.41% | Eyes 50% |
| 8:00 PM | 77.9 | 6.60% | 58.23 | 45.41% | open/50% |
| 8:05 PM | 78.35 | 7.29% | 60.3 | 52.79% | closed. |
| 8:16 PM | 78.86 | | 63.36 | | |
| Test 2: Pleasanton, CA, Apr. 20, 2003 | | | | | |
| 8:33 PM | 75 | 8.00% | 44.4 | 51.37% | Warmcloth |
| 8:40 PM | 81 | 8.00% | 67.21 | 58.76% | onfacefors |
| 8:43 PM | 81 | | 70.49 | | minutes. Eyes closed. |
| Test 3: Pleasanton, CA, Apr. 21, 2003 | | | | | |
| 3:50 PM | 74.45 | 3.43% | 43.78 | 3.47% | No moisture |
| | | 12.49% | 45.3 | 58.70% | added, eyes |
| | | 4.62% | 69.48 | 80.45% | closed. |
| | | 8.11% | 79 | 83.90% | |
| | | | 80.51 | | |
| 3:58 PM | 77 | | | | Warm, moist |
| 4:20 PM | 83.75 | | | | moisture |
| 4:40 PM | 77.89 | | | | pads |
| 4:55 PM | 80.49 | | | | inserted for 10minutes. |
| Test 4: Pleasanton, CA, Apr. 22, 2003 | | | | | |
| 7:30 PM | 70 | | 48 | | Warm, moist |
| 7:35 PM | 71 | 1.43% | 65 | 35.42% | moisture |
| 7:40 PM | 71 | 1.43% | 70 | 45.83% | pads |
| 7:50 PM | 70 | 0.00% | 74.7 | 55.63% | inserted. |
| 8:00 PM | 70 | 0.00% | 78 | 62.50% | Eyes closed. |
| Test 5: New York, NY, Apr. 24, 2003 | | | | | |
| 10:21 | 63.74 | | 26.63 | | Warm, moist |
| 10:40 | 71 | 11.39% | 66 | 147.84% | moisturepads |

TABLE 1-continued

Testing of Apparatus on Subjects with Normal Eyes

| Time | Temperature | % Change from Base Temperature | Relative Humidity (RH) | % Change from Base RH | Comments |
|---|---|---|---|---|---|
| 10:50 | 71 | 11.39% | 72 | 170.37% | insertedfor5 minutes. Eyes closed. |
| Test 6: New York, NY, Apr. 25, 2003 | | | | | |
| 8:15 PM | 70 | 4.29% | 35 | 91.43% | Generous |
| 8:30 PM | 73 | 4.29% | 67 | 108.57% | spray of |
| 8:40 PM | 73 | 5.71% | 73 | 114.29% | Nature's |
| 8:45 PM | 74 | 5.71% | 75 | 122.86% | Tears eye |
| 8:51 PM | 74 | 5.71% | 78 | 125.71% | mistadded. |
| 9:00 PM | 74 | | 79 | | |

The results of the testing of the apparatus and system of the present invention on subjects with dry eye conditions are depicted in Table 2 below. As Table 2 depicts, the temperature and relative humidity increased over time during each test. Notably, the longer the subject wore the apparatus of the present invention, the greater the temperature and humidity increased. Additionally, patients who participated in the tests experienced significant relief from their dry eye conditions for up to six hours following the use of the present invention.

TABLE 2

Testing of Apparatus on Subjects with Dry Eye Conditions

| Time | Temperature | % Change from Base Temperature | Relative Humidity (Ru) | % Change from Base RH | Comments |
|---|---|---|---|---|---|
| Test 7: Campbell, CA, May 29, 2003 | | | | | |
| 6:20 PM | 74 | | 44 | | Added |
| 6:26 PM | 76 | 2.70% | 62 | 40.91% | Moisture |
| 6:30 PM | 75 | 1.35% | 70.2 | 59.55% | Pad |
| 6:35 PM | 76 | 2.70% | 72 | 63.64% | Removed |
| 6:40 PM | 76 | 2.70% | 74 | 68.18% | Moisture |
| 6:45 PM | 77 | 4.05% | 77.54 | 76.23% | Pad |
| Test 8: Campbell, CA, May 29, 2003 | | | | | |
| 7:02 PM | 74 | | 46 | | Added |
| 7:07 PM | 75.5 | 2.03% | 63.6 | 38.26% | Moisture Pads |
| 7:14 PM | 78 | 5.41% | 67 | 45.65% | Removed |
| 7:22 PM | 77 | 4.05% | 73 | 58.70% | Moisture |
| 7:28 PM | 77.4 | 4.59% | 76 | 65.22% | Pads |
| Test 9: Campbell, CA, May 29, 2003 | | | | | |
| 7:56 PM | 73 | | 45 | | Added |
| 8:05 PM | 76 | 4.11% | 78 | 73.33% | Moisture Pads |
| 8:08 PM | 76 | 4.11% | 81.1 | 80.22% | Removed |
| 8:14 PM | 78.44 | 7.45% | 85.82 | 90.71% | Moisture |
| 8:19 PM | 79 | 8.22% | 85.03 | 88.96% | Pads |
| 8:25 PM | 80 | 9.59% | 86.6 | 92.44% | |

The results of testing the apparatus and system of the present invention on subjects in a low-humidity environment, i.e., on an airplane, are depicted in Table 3 below. As Table 3 depicts, the temperature and relative humidity increased over time for each test. Notably, the relative humidity increased by over 100% for each test. Additionally, the relative humidity of the area surrounding the eyes continued to increase, even while the relative humidity within the plane continued to decline, even upon descent of the airplane.

TABLE 3

Testing of Apparatus on Subjects with Dry Eye Conditions

| Time | Temperature | % Change from Base Temperature | Relative Humidity (RH) | % Change from Base RH | Comments |
|---|---|---|---|---|---|
| TEST 10: Airplane, June 18 | | | | | |
| 10:01 AM | 74 | | 21 | | Added little |
| 10:11 AM | 76 | 2.70% | 52 | 147.62% | moistureto lens cavity (1 drop, spread around lens cavity) 10 minutes at 10,000 ft. |
| Test 11: Airplane, Jun. 18, 2003 | | | | | |
| 10:23 AM | 74 | | 17.1 | | Sprayedeyes |
| 10:40 AM | 77 | 4.05% | 61 | 256.73% | lightly with Biomist 13 minutes at 10,000 ft. |

As evident from the data of Tables 1, 2, and 3 the present invention fulfills a long-felt need in the industry to treat and/or alleviate dry eye symptoms while at the same time promoting healthy eyes. The present invention overcomes various shortcomings of the currently available treatments, including providing a natural, inexpensive, easy to use and comfortable device that can be used in the treatment of dry eye conditions and to promote overall eye health.

Although the invention has been described with respect to particular embodiments thereof, it should be realized that various changes and modifications may be made therein without departing from the spirit and scope of the invention. While the invention as shown in the drawings and described in detail herein discloses arrangements of elements of particular construction and configuration for illustrating preferred embodiments of structure and method of operation of the present invention, it is to be understood, however, that elements of different construction and configuration and other arrangements thereof, other than those illustrated and described, may be employed in accordance with the spirit of this invention. Any and all such changes, alternations and modifications as would occur to those skilled in the art are considered to be within the scope of this invention as broadly defined in the appended claims.

Further, the purpose of the attached abstract is to enable the U.S. Patent and Trademark Office and the public generally, and especially the scientists, engineers and practitioners in the art who are not familiar with patent or legal terms or phraseology to determine quickly from a cursory inspection the nature and essence of the technical disclosure of the application. The abstract is neither intended to define the invention of the application, which is measured by the claims, nor is it intended to be limiting as to the scope of the invention in any way.

What is claimed is:

1. An eyewear apparatus for treating dry eye conditions comprising:
   a pair of eyecups, each said eyecup having a soft, pliable, curved lens projecting from a circumferential edge, said circumferential edge having a rear surface;
   each said eyecup having an interior cavity defined by a first surface of said lens communicating along said circumferential edge with in said rear surface;
   a sidewall disposed in said interior cavity;
   at least one moisture pad, said moisture pad having two side surfaces terminating at a perimeter edge;
   said sidewall adapted for removable engagement with said perimeter edge of said moisture pad when inserted in said interior cavity into an engaged position;
   a bridge coupling said eyecups;
   a soft, pliable gasket on said rear surface of each of said pair of eyecups, said gasket designed to substantially encircle and contact facial skin adjacent to the orbital bone of a respective eye socket of the wearer when said eyewear apparatus is in an as-worn position being worn by a user;
   said moisture pad and having an ocular cavity communicating with at least one of said two surfaces;
   said ocular cavity dimensioned to accommodate a respective eye of said user therein when said moisture pad is in said engaged position and said eyewear apparatus is in said as-worn position; and
   means to maintain said eyewear apparatus in said as-worn position.

2. The eyewear apparatus of claim 1, further comprising:
   a pair of said moisture pads; and
   each respective ocular cavity of said pair of moisture pads being in a substantially sealed communication with a respective eye of said user, when said eyewear apparatus is in said as-worn position, whereby each respective eye of said user has a separate respective said ocular cavity in substantially sealed communication therewith.

3. The eyewear apparatus of claim 2, further comprising:
   each said moisture pad formed of resilient material which biases against compression; and
   said perimeter edge of each said moisture pad having a circumference dimensioned to provide a biased engagement to said sidewall thereby providing removable biased engagement of said moisture pad in said engaged position.

4. The eyewear apparatus of claim 2, further comprising:
   a first of said two side surfaces, having a circumference larger than a second of said side surfaces thereby forming a slanted said perimeter edge;
   said ocular cavity communicating with at least said second of said side surfaces;
   said sidewall slating from a widest point closest to said lens, to a narrower point closest to said rear surface; and
   whereby said perimeter edge when engaged with said sidewall provides means for removable engagement of said moisture pad in said interior cavity.

5. The eyewear apparatus of claim 2, further comprising:
   means to communicate temperature change to said ocular cavity; and
   means to removably engage said means to communicate temperature change to said ocular cavity, within said interior cavity.

6. The eyewear apparatus of claim 5 wherein said means to communicate temperature change to said ocular cavity is a component having dimensions to fit within said interior cavity, said component formed one of a group of components for temperature change consisting of microwaveable or refrigerateable gel packs, stones, ceramics, chemically activated hot and cold packs, and said moisture pad being formed of material which may be heated or chilled.

7. The eyewear apparatus of claim 6 wherein said means to removably engage said means to communicate temperature change to said ocular cavity, within said interior cavity, is an engagement cavity formed in said moisture pad, said engagement cavity in said moisture pad adapted to removably engage said component therein.

8. The eyewear apparatus of claim 5 wherein said means to removably engage said means to communicate temperature change to said ocular cavity, within said interior cavity, is an engagement cavity formed in said moisture pad, said engagement cavity in said moisture pad adapted to removably engage said component therein.

9. The eyewear apparatus of claim 1, further comprising:
   said moisture pad formed of resilient material which biases against compression; and
   said perimeter edge of said moisture pad having a circumference dimensioned to provide a biased engagement to said sidewall thereby providing removable biased engagement of said moisture pad in said engaged position.

10. The eyewear apparatus of claim 1, further comprising:
    a first of said two side surfaces, having a circumference larger than a second of said side surfaces thereby forming a slanted said perimeter edge;
    said ocular cavity communicating with at least said second of said side surfaces;
    said sidewall slating from a widest point closest to said lens, to a narrower point closest to said rear surface; and
    whereby said perimeter edge when engaged with said sidewall provides means for removable engagement of said moisture pad in said interior cavity.

11. The eyewear apparatus of claim 1, further comprising:
    means to communicate temperature change to said ocular cavity; and
    means to removably engage said means to communicate temperature change to said ocular cavity, within said interior cavity.

12. The eyewear apparatus of claim 11 wherein said means to communicate temperature change to said ocular cavity is a component having dimensions sized to fit within said interior cavity, said component formed one of a group of components for temperature change consisting of microwaveable or refrigerateable gel packs, stones, ceramics, chemically activated hot and cold packs, and said moisture pad being formed of material which may be heated or chilled.

13. The eyewear apparatus of claim 12 wherein said means to removably engage said means to communicate temperature change to said ocular cavity, within said interior cavity, is an engagement cavity formed in said moisture pad, said engagement cavity in said moisture pad adapted to removably engage said component therein.

14. The eyewear apparatus of claim 11 wherein said means to removably engage means to removably engage said means to communicate temperature change to said ocular cavity, within said interior cavity, is an engagement cavity formed in said moisture pad, said engagement cavity in said moisture pad adapted to removably engage said component therein.

15. The eyewear apparatus of claim 11 wherein said means to removably engage means to removably engage said means to communicate temperature change to said ocular cavity, within said interior cavity, is an engagement cavity formed by a gap defined by the area between one of said two side surfaces and said first surface of said lens.

16. The eyewear apparatus of claim 15, further comprising:
both said moisture pads having an ocular cavity communicating with at both of said two surfaces, and
said ocular cavity communicating with said engagement cavity.

17. The eyewear apparatus of claim 1 wherein said means to maintain said eyewear apparatus in said as-worn position is a strap.

18. The eyewear apparatus of claim 1, further comprising:
said moisture pads being members of a kit having a plurality of said moisture pads, each member of said kit having different treatment characteristics provided by scents or medicinal purpose, whereby said eyewear apparatus can be customized for the treatment provided to each individual eye of a user, by engaging the member of said kit having desired treatment characteristics.

19. The eyewear apparatus of claim 1 wherein said gasket is formed by a projection extending from said moisture pad.

20. The eyewear apparatus of claim 1, further comprising:
said moisture pad having an ocular cavity communicating with at both of said two surfaces.

21. An eyewear apparatus for treating dry eye conditions comprising:
a pair of eyecups, each said eyecup having a soft, pliable, curved lens projecting from perimeter edge portion, said perimeter edge portion having a rear surface;
a bridge coupling said eyecups;
each said eyecup having an interior cavity defined by and area within a first surface of said lens portion projecting from a communication with said perimeter edge portion;
each said eyecup having a sidewall disposed upon said first surface;
a pair moisture pads, each of said moisture pads having two side surfaces terminating at a perimeter side edge, and each having an ocular cavity communicating with at least one of said two surfaces;
said perimeter side edge of each of said moisture pads adapted for removable biased engagement with said sidewall to removably mount said moisture pads in an engaged position;
said rear surface of said eyecups dimensioned to substantially encircle and contact facial skin adjacent to the orbital bone of a respective eye socket of the wearer when said eyewear apparatus is positioned in an as-worn position where it is being worn by a user; and
means to maintain said eyewear apparatus in said as-worn position, whereby each respective ocular cavity of said pair of moisture pads is in a substantially sealed communication with a separate respective eye of said user when said eyewear apparatus in said as-worn position.

22. The eyewear apparatus of claim 21, further comprising:
a soft, pliable gasket on said rear surface of each of said pair of eyecups.

23. The eyewear apparatus of claim 21, further comprising:
means to communicate temperature change to said ocular cavity; and
means to removably engage said means to communicate temperature change to said ocular cavity, within said interior cavity.

24. The eyewear apparatus of claim 23, wherein said means to removably engage said means to communicate temperature change within said interior cavity comprises:
forming said means to communicate temperature change into a temperature component, said temperature component dimensioned to engage in a cavity formed in said moisture pads or between said moisture pads and said first surface.

* * * * *